(12) United States Patent
Hadoux et al.

(10) Patent No.: US 11,963,721 B2
(45) Date of Patent: Apr. 23, 2024

(54) METHOD AND SYSTEM FOR QUANTIFYING BIOMARKER OF A TISSUE

(71) Applicant: Centre for Eye Research Australia Limited, East Melbourne (AU)

(72) Inventors: Xavier Hadoux, East Melbourne (AU); Flora Hui, East Melbourne (AU); Peter Van Wijngaarden, East Melbourne (AU); Jonathan Guy Crowston, East Melbourne (AU)

(73) Assignee: Centre For Eye Research Australia Limited, East Melbourne (AU)

( * ) Notice: Subject to any disclaimer, the term of this patent is extended or adjusted under 35 U.S.C. 154(b) by 879 days.

(21) Appl. No.: 16/961,333

(22) PCT Filed: Jan. 11, 2019

(86) PCT No.: PCT/AU2019/000003
§ 371 (c)(1),
(2) Date: Jul. 10, 2020

(87) PCT Pub. No.: WO2019/136513
PCT Pub. Date: Jul. 18, 2019

(65) Prior Publication Data
US 2020/0375521 A1  Dec. 3, 2020

Related U.S. Application Data

(60) Provisional application No. 62/616,240, filed on Jan. 11, 2018.

(30) Foreign Application Priority Data

Apr. 20, 2018  (AU) .............................. 2018901319

(51) Int. Cl.
*A61B 3/10* (2006.01)
*A61B 3/12* (2006.01)
(Continued)

(52) U.S. Cl.
CPC ................. *A61B 3/10* (2013.01); *A61B 3/12* (2013.01); *A61B 3/14* (2013.01); *A61B 5/0075* (2013.01);
(Continued)

(58) Field of Classification Search
CPC .... A61B 3/10; A61B 3/12; A61B 3/14; A61B 5/0075; A61B 5/14507; A61B 5/1455;
(Continued)

(56) References Cited

U.S. PATENT DOCUMENTS 8,879,813 B1  11/2014  Solanki et al.
2004/0063216 A1*  4/2004  Lubocki ................ A61B 5/411
436/173

(Continued)

FOREIGN PATENT DOCUMENTS

JP  2010-507412 A  3/2010
JP  2016-5133475 A  10/2016
(Continued)

OTHER PUBLICATIONS

International Search Report and Written Opinion for Application No. PCT/AU2019/000003 dated Mar. 28, 2019.
(Continued)

*Primary Examiner* — James R Greece
(74) *Attorney, Agent, or Firm* — Alston & Bird LLP

(57) ABSTRACT

The present disclosure relates to a method and a system for quantifying a biomarker of a biological tissue. Two spectral sub-intervals are determined from a plurality of images of the tissue acquired at discrete wavelengths within a main wavelength interval using an imaging sensor in a manner such that the combination of the image data in the at least two spectral sub-intervals are correlated with a clinical variable of interest. The tissue is illuminated using one or more light sources with wavelengths within the at least two
(Continued)

spectral sub-intervals. A measurement is of the light reflected by the tissue is acquired using an imaging sensor; and a measure of the biomarker of the tissue is calculated using the acquired measurement. The main wavelength interval is broader than each of the at least two spectral sub-intervals and at least one spectral confounder causing a spectral variability of the acquired image is present in the tissue.

21 Claims, 21 Drawing Sheets

(51) Int. Cl.
*A61B 3/14* (2006.01)
*A61B 5/00* (2006.01)
*A61B 5/145* (2006.01)
*A61B 5/1455* (2006.01)
*A61B 6/03* (2006.01)
*G01J 3/02* (2006.01)
*G06V 10/143* (2022.01)
*G06V 10/60* (2022.01)
*G06V 20/69* (2022.01)
*G06V 40/18* (2022.01)
*G16H 10/40* (2018.01)
*G16H 30/40* (2018.01)
*G16H 50/20* (2018.01)
*G16H 70/60* (2018.01)
*G06V 10/58* (2022.01)

(52) U.S. Cl.
CPC ........ *A61B 5/14507* (2013.01); *A61B 5/1455* (2013.01); *A61B 5/4088* (2013.01); *A61B 5/7264* (2013.01); *A61B 6/037* (2013.01); *G01J 3/0229* (2013.01); *G06V 10/143* (2022.01); *G06V 10/60* (2022.01); *G06V 20/693* (2022.01); *G06V 20/695* (2022.01); *G06V 40/18* (2022.01); *G16H 10/40* (2018.01); *G16H 30/40* (2018.01); *G16H 50/20* (2018.01); *G16H 70/60* (2018.01); *G06V 10/58* (2022.01)

(58) Field of Classification Search
CPC ..... A61B 5/4088; A61B 5/7264; A61B 6/037; G16H 70/60; G16H 10/40; G16H 50/20; G16H 30/40; G06V 20/695; G06V 10/60; G06V 10/143; G06V 40/18; G06V 20/693; G01J 3/0229
USPC ................................ 351/200, 205, 206, 246
See application file for complete search history.

(56) References Cited

U.S. PATENT DOCUMENTS

| | | |
|---|---|---|
| 2008/0306337 A1 | 12/2008 | Livingston et al. |
| 2009/0225277 A1 | 9/2009 | Gil |
| 2011/0080581 A1 | 4/2011 | Bhargava et al. |
| 2012/0101371 A1 | 4/2012 | Verdooner |
| 2014/0378843 A1* | 12/2014 | Valdes ............... A61B 1/063 600/476 |
| 2015/0044098 A1 | 2/2015 | Smart et al. |
| 2015/0323384 A1 | 11/2015 | Bird et al. |
| 2017/0065179 A1 | 3/2017 | Smith |
| 2019/0365235 A1* | 12/2019 | Di Tullio ............ A61B 5/7221 |
| 2020/0051259 A1* | 2/2020 | Sylvestre ............ A61B 5/6821 |

FOREIGN PATENT DOCUMENTS

| | | |
|---|---|---|
| WO | WO 2007/032224 A1 | 3/2007 |
| WO | WO 2009/146425 A1 | 3/2009 |
| WO | WO 2010/019515 A2 | 2/2010 |
| WO | WO 2013/086516 A1 | 6/2013 |
| WO | WO 2014/105521 A1 | 7/2014 |
| WO | WO 2016/069788 A1 | 5/2016 |

OTHER PUBLICATIONS

IN 202017033170 Examination Report dated Apr. 27, 2022, English Translation.
EP 19737964 Supplemental European Search Report and Search Opinion dated Sep. 10, 2021.
Lu, et al., "Medical hyperspectral imaging: a review," Journal of Biomedical Optics, 19(1), 010901, (Jan. 2014).
JP 2020-535598 Office Action dated Aug. 2, 2022, English Translation.
CN 201980008015.3 1$^{st}$ Office Action dated Oct. 31, 2022.
IL 275840 Examination report dated Jul. 11, 2023.
AU 2019207516 Examination report dated Sep. 18, 2023.

* cited by examiner

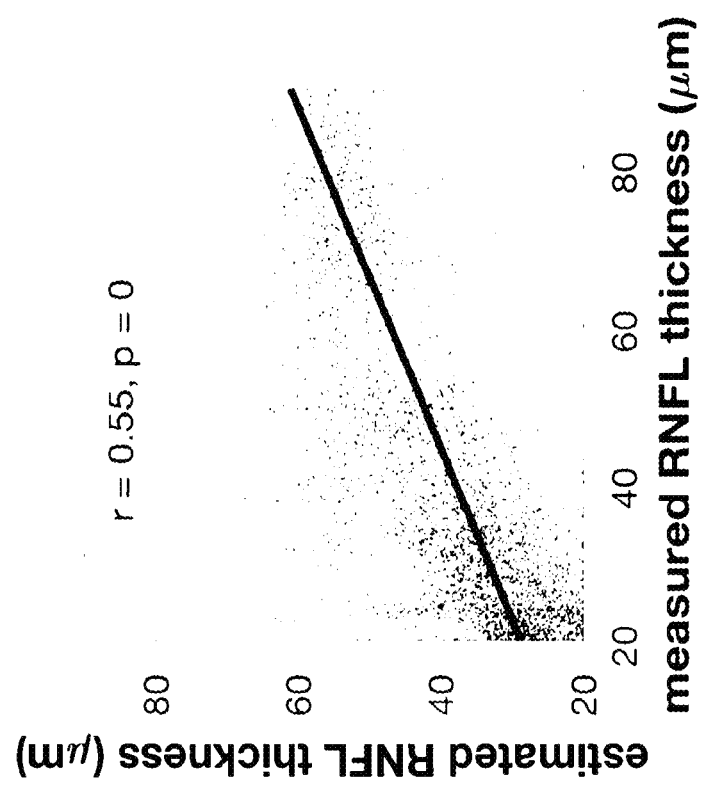
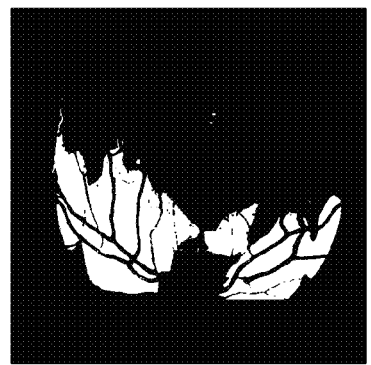
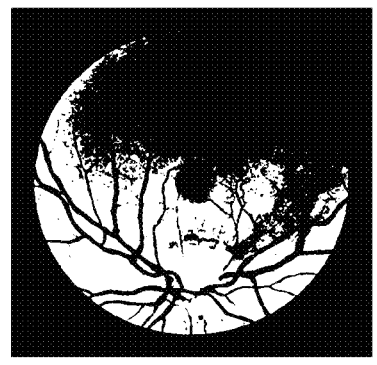
FIGURE 18A
FIGURE 18B
FIGURE 18C

METHOD AND SYSTEM FOR QUANTIFYING BIOMARKER OF A TISSUE

CROSS-REFERENCE TO RELATED APPLICATIONS

This application is a national stage application filed under 35 U.S.C. § 371 of International Application No. PCT/AU2019/000003 filed Jan. 11, 2019, which application claims priority to U.S. Provisional Application Ser. No. 62/616,240 filed Jan. 11, 2018 and Australian Application No. 2018901319 filed Apr. 20, 2018. Each of the foregoing applications is hereby incorporated by reference herein in its entirety.

TECHNICAL FIELD

The present disclosure relates to the field of diagnosing a medical condition, or determining the effect of aging, based on imaging of tissue. More specifically, the present disclosure relates to methods and systems for quantifying a biomarker a biological tissue using imaging and image data processing algorithms.

BACKGROUND

Imaging techniques are commonly used to assist in the detection and diagnosis of various illnesses. Images of biological tissues of a subject are analyzed to quantify their physiological parameters in view of detecting anomalies. A commonly used technique to detect amyloid and other anomalies comprises positron emission tomography (PET) scanning. PET scans are expensive, time consuming, and may cause discomfort to the subject.

For example, the presence of abnormal amyloid in the retina of a patient can be used to diagnose a condition of the retina. In particular, it has been shown that the presence of amyloid in the retina of a subject may indicate the onset of Alzheimer's disease. It has also been proposed that the diagnosis of other illnesses, for example glaucoma, diabetes, diabetic retinopathy, hypertension, cardiovascular disease, cerebrovascular disease, macular degeneration, Parkinson's disease, other amyloidopathies and other tauopathies could be based on the detection of anomalies within the retina of a subject.

Recently, techniques that involve both visual analysis and numerical image processing of hyperspectral images of the eye have been proposed to detect a manifestation of a disease rooted in other organs of the subject.

The quantitative analysis of biomarkers based on hyperspectral images of biological tissues, in particular images of the eye, is a very promising tool for the diagnosis of several health conditions. However, the commercial systems used to acquire hyperspectral images remain very expensive and not easily accessible.

SUMMARY

Embodiments of the present invention provide techniques for quantifying a biomarker of a tissue using imaging and image data processing algorithms. In particular, aspects of the invention provide systems and methods to acquire and process hyperspectral image data from a biological tissue and quantify a biomarker in a tissue associated with a disease. Further aspects of the invention provide systems and methods to acquire multispectral image data from a tissue and process the image data to quantify the biomarker.

In accordance with a first aspect, the present invention provides a method for quantifying a biomarker of a tissue, the method comprising:
    acquiring a plurality of images of the tissue at discrete wavelengths within a main wavelength interval using an imaging sensor;
    determining, using a processor, at least two spectral sub-intervals in a manner such that combination of the image data in the at least two spectral sub-intervals is correlated with a clinical variable of interest; and
    calculating a measure of the biomarker of the tissue using the image data in the at least two spectral sub-intervals using the processor;
    wherein the main wavelength interval is broader than each of the at least two spectral sub-intervals and at least one spectral confounder causing a spectral variability of the acquired image is present in the tissue.

In accordance with a second aspect, the present invention provides A method for quantifying a biomarker of a tissue, the method comprising:
    determining, using a processor, at least two spectral sub-intervals from a plurality of images of the tissue acquired at discrete wavelengths within a main wavelength interval using an imaging sensor in a manner such that the combination of the image data in the at least two spectral sub-intervals is correlated with a clinical variable of interest;
    illuminating the tissue using one or more light sources with wavelengths within the at least two spectral sub-intervals;
    acquiring a measurement of the light reflected by the tissue using an imaging sensor; and
    calculating a measure of the biomarker of the tissue using the acquired measurement;
    wherein the main wavelength interval is broader than each of the at least two spectral sub-intervals and at least one spectral confounder causing a spectral variability of the acquired image is present in the tissue.

In an embodiment, the clinical variable of interest comprises any one or a combination of a disease, a severity or subtype of disease, a known biomarker or a physiological state.

In an embodiment, the main wavelength interval is such that the acquired images represent a hyperspectral or multispectral representation of the tissue.

In an embodiment, the method comprises acquiring a plurality of images comprises using one or more cameras operating at different wavelengths.

In an embodiment, the method comprises extracting a spectral parameter for each of the at least two spectral sub-intervals to form a multispectral representation of the tissue.

In an embodiment, the method comprises identifying at least one spectral confounder causing a spectral variability in the acquired images.

In an embodiment, determining at least two spectral sub-intervals is performed in a manner such that the spectral information of the combination of the at least two spectral sub-intervals and the spectral confounder are orthogonal, uncorrelated or independent.

In an embodiment, determining at least two spectral sub-intervals is performed by applying a band selection method, a machine learning algorithm or an artificial intelligence engine.

In an embodiment, the variable of interest comprises the amount or distribution of amyloid beta measured in a brain using positron emission tomography (PET), or measured in cerebrospinal fluid (CSF).

In an embodiment, determining at least two spectral sub-intervals comprises using a multivariate statistics, machine learning or artificial intelligence techniques.

In an embodiment, calculating a measure of the biomarker uses multivariate statistics, machine learning or artificial intelligence techniques.

In an embodiment, the multivariate statistics include regression, logistic regression or discrimination.

In an embodiment, the machine learning or artificial intelligence techniques account for demographic information, clinical information, other variables of interest or multiple regions of interest in the image data.

In an embodiment, determining at least two spectral sub-intervals is performed by a machine learning algorithm that transforms multispectral data into a score that represents the biomarker.

In an embodiment, the method comprises applying an optical filter to the one or more light sources.

In an embodiment, the method comprises applying an optical filter along a light path of the light generated by the one or more light sources.

In an embodiment, the tissue is the retina of a person and the optical filter is embedded within a contact lens applied on an eye of the person.

In accordance with the second aspect, the present invention provides a system for quantifying a biomarker of a tissue, the system comprising:
    an optical assembly comprising one or more light sources, the optical assembly being arranged to illuminate a portion of the tissue at wavelengths within at least two predetermined spectral intervals; and
    an imaging assembly comprising an imaging sensor arranged to receive light reflected from the portion of the tissue and translate the light to digital data;
    wherein the at least two predetermined spectral sub-intervals are specific to a known variable of interest.

In an embodiment, the system comprises a biomarker selection assembly arranged to select the at least two light spectral intervals based on a user selected biomarker of a tissue.

In an embodiment, the system comprises a processing module arranged to receive data from the imaging sensor and being configured to:
    combine and process the data received from the imaging sensor to extract spectral information and form a multispectral representation of the tissue; and
    process the multispectral representation of the tissue to quantify the biomarker.

In an embodiment, the tissue is a portion of the retina and the biomarker is a measure of amyloid beta (AB) for predicting/stratifying risk, screening or diagnosing Alzheimer's disease and the at least two spectral intervals consist of three wavebands located within about 100 nm of 475 nm, within about 100 nm of 545 nm, and within about 100 nm of 725 nm, and each with a bandwidth under about 200 nm.

In an embodiment, the optical assembly is arranged to generate light with a spectrum within the at least two spectral intervals.

In an embodiment, the illumination assembly comprises optical filters arranged to filter the generated light path or the reflected light path within the at least two sub-spectral intervals.

In an embodiment, the tissue is a portion of the retina and the variable of interest is brain or cerebrospinal fluid amyloid beta level related to Alzheimer's disease and the at least two spectral intervals consist of three wavebands located within about 100 nm of 475 nm, within about 100 nm of 545 nm, and within about 100 nm of 725 nm, and each with a bandwidth under about 200 nm.

In accordance with the third aspect, the present invention provides a method for quantifying a biomarker of a tissue, the method comprising:
    acquiring a hyperspectral image of the tissue using an imaging sensor within a contiguous wavelength interval;
    identifying at least one spectral confounder causing a spectral variability of the hyperspectral image;
    deriving a spectral model of the tissue in a manner such that the correlation of the spectral model and the identified spectral confounder is minimized; and
    calculating a measure of the biomarker of the tissue using the derived spectral model.

In an embodiment, the spectral model of the tissue is derived to be orthogonal, uncorrelated or independent to the identified spectral confounder.

In an embodiment, the spectral model is derived from the main spectral difference between two groups, each group having a distinct amount of the variable of interest.

In an embodiment, deriving a spectral model of the tissue comprises deriving a clean hyperspectral representation of the tissue by processing the hyperspectral representation of the tissue and a spectral signature of the at least one spectral confounder in a manner such that the clean hyperspectral representation of the tissue has reduced variability caused by the spectral signature of the at least one spectral confounder.

In an embodiment, acquiring an hyperspectral image of the tissue comprises sequentially illuminating the tissue, using one or more light sources, with monochromatic or narrow bandwidth light within a contiguous predetermined range of wavelengths and, for each wavelength, using the imaging sensor to acquire a measurement of the light reflected by the tissue.

In an embodiment, identifying at least one spectral confounder comprises reading from a spectral database one or more spectral profiles of spectral confounders and processing the spectral information from the hyperspectral image and the one or more spectral profile.

In an embodiment, deriving a clean hyperspectral representation comprises removing, from the spectral information, a spectral variability caused by the spectral profile of the at least one spectral confounder.

In an embodiment, identifying at least one spectral confounder comprises using a specific spectral confounder as a reference cofounder and calculating a delta hyperspectral image which represents a pixel-by-pixel and wavelength-by-wavelength difference between two hyperspectral images.

In an embodiment, the spectral information is processed in accordance with the following steps:
    computing the inter-class spectral variability between groups that differ with respect to the variable of interest;
    extracting a first set of principal eigenvectors of the intra-class spectral database; and
    removing one or more eigenvectors using an orthogonal projection to produce an intermediate dataset in which the intra-class variability is substantially removed;

wherein the biomarker is quantified using a spectral dimension reduction based on the clean spectral representation of the tissue.

In an embodiment, the spectral information is processed in accordance with the following steps:

computing the inter-class spectral variability between distinct groups of the spectral database;

extracting a first set of principal eigenvectors of the inter-class variability between the distinct groups;

removing the inter-class variability using an orthogonal projection based on the first set of principal eigenvectors from a combination of the distinct groups to produce an intermediate dataset in which the inter-class variability is substantially removed;

computing intra-class variability within the intermediate dataset; extracting a second set of principal eigenvectors of the intra-class variability of the intermediate dataset; and extracting a third set of principal eigenvectors of a plurality of clean spectral presentations in the statistical database;

wherein removing, from the interim spectral information, the spectral variability caused by the at least one non-specific confounder comprises removing, from the interim spectral information, the intra-class variability using an orthogonal projection based on the second set of principal eigenvectors to create the clean spectral representation of the tissue; and wherein the biomarker is quantified using a projection based on the third set of principal eigenvectors on the clean spectral representation of the tissue.

In an embodiment, the at least one spectral confounder comprises at least one ocular confounder and the quantified biomarker indicates the presence or absence of a variable of interest in the retina of the person.

In an embodiment, the at least one ocular spectral confounder is comprised of variations in melanin content, cataract, discolouration of the lens, hemoglobin content, retinopathy, retinal pigment epithelial thickness or density, RNFL thickness, choroidal thickness, macular pigment content and/or a combination thereof.

In accordance with a fifth aspect, the present invention provides a system for quantifying a biomarker of a tissue, the system comprising:

an illumination assembly arranged to successively illuminate a portion of a tissue with monochromatic or narrow bandwidth light within a contiguous range of wavelengths;

an imaging assembly comprising an imaging sensor arranged to receive light reflected by the portion of the tissue and translate the light to digital data; and a processing module and a memory module arranged to receive data from the imaging sensor and being configured to execute instructions to perform a method in accordance with the fourth aspect.

The present invention is suitable for any measuring any biomarker that is indicative of a disease state or predisposition for a disease. Examples include, but not limited to, amyloid beta for Alzheimer's, varying levels of cataract and melanin content in the retina within the subject (within the eye and between the two eyes), and between subjects, amyloid beta in the brain measured by PET scan, or amyloid beta in the cerebrospinal fluid, RNFL thickness, retinal thickness, blood within or beneath the retina.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which:

FIG. 10 shows a schematic diagram of a system for quantifying a biomarker of a biological tissue, based on multispectral imaging;

FIG. 18 shows an image of the retinal nerve fibre layer (RNFL) thickness measured by OCT (A), an image of the RNFL thickness estimated using MS imaging with three spectral intervals (B), and a graph showing the correlation between RNFL thickness measured by OCT versus thickness estimated using MS imaging (C);

DETAILED DESCRIPTION

Various aspects of the present disclosure generally address one or more of the problems related to the presence of confounders that may impair the performance of medical imaging techniques.

Broadly stated, a confounder, also called a confounding factor, can be any factor that impacts the content and/or quality of a biometric measurement when this factor is not directly related to the quantity or variable that is intended to be measured. In the particular case of hyperspectral (HS) or multispectral (MS) imaging of the retina of a subject, where it is desired to acquire spectral information about the retina or about a part of the retina, various factors present in the eye of the subject may impact this spectral information. For example, a subject having blue eyes has very little melanin in the stroma of his/her iris and fundus. In contrast, the stroma of a subject having brown eyes has a high melanin content. The melanin content tends to alter the spectral content of the HS image, this alteration being unrelated to the actual condition of the retina. Without limitation, other confounders may include cataract, discolouration of the lens, blood hemoglobin levels and thickness, retinopathy, spectral density, RNFL thickness, and macular pigment content. A given subject may have any number of these confounders.

One aspect of the technology described herein involves obtaining a hyperspectral image of a biological tissue, for example the retina of a subject, and alleviating the effects of one or more potential ocular confounders on this image by using statistical information obtained from a plurality of subjects, some of whom having similar spectral confounders. A spectral representation of the biological tissue is obtained in view of quantifying a biomarker, for example in view of determining the presence of amyloid beta in the retina of a subject. Alternatively, a multispectral image of a biological tissue, for example the retina of a subject can be taken by selecting appropriate wavelength intervals that allow alleviating the effects of one or more potential ocular confounders. Numerical parameters are associated with each spectral interval to quantify a physiological parameter, for example in view of determining the presence of amyloid beta in the retina of a subject.

In Alzheimer's disease (AD), for example, a protein called amyloid beta accumulates in the brain and in the eye over many years. While there are tests that can be used to confirm a diagnosis of AD once memory impairment occurs, these tests are costly, not widely available and invasive. None of these tests are used to screen people without memory impairment to identify those at risk of the disease. This is important as if treatments are to be effective for AD, it is likely that they need to be started before the disease is too advanced.

Figure 1:
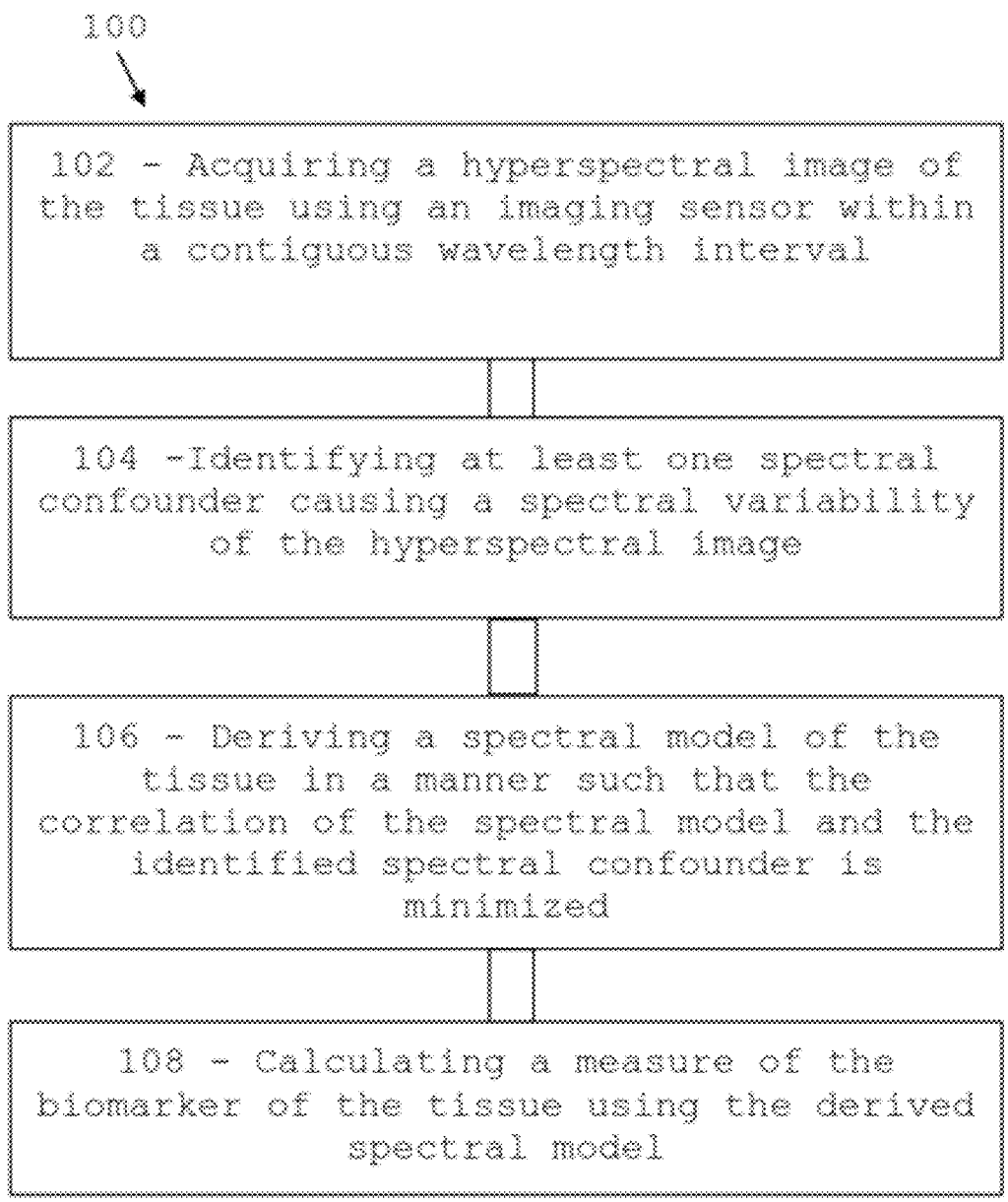
FIG. 1 shows a flow diagram with method steps used to quantify a biomarker of a tissue based on hyperspectral imaging.

Referring now to FIG. 1 there is shown a flow diagram 100 with method steps used to quantify a biomarker of a tissue starting from a HS images. At step 102, at least one hyperspectral image of the tissue is acquired using an imaging sensor within a contiguous wavelength interval. At step 104, at least one spectral confounder causing a spectral variability of the hyperspectral image is identified. At step 106, a spectral model of the tissue is derived in a manner such that the correlation of the spectral model and the identified spectral confounder is minimized. At step 108, a measure of the biomarker of the tissue is calculated using the derived spectral model.

A preferred way of deriving the spectral model required the calculation of a clean HS representation of the biological tissue. This representation can be calculated by processing the HS data with a spectral signature of the at least one spectral confounder with the aim of minimising the variability caused by the spectral signature of the at least one spectral confounder.

The HS image comprises a plurality of images of the retina of the subject, each of the images being obtained at a distinct wavelength. The image may be pre-processed and the pre-processing can include, for example, a normalization of light intensities at the various wavelengths of the HS image. Image registration may take place to ensure that pixels of images taken at any given wavelength are aligned with corresponding pixels of images taken at any other wavelength so that corresponding pixels represent a same element of the retina of the subject. The registration can overcome misalignments caused by a movement of the eye of the subject as the images are taken at the various wavelengths. Co-registration between images of the retina of the subject taken at different times may take, for example, when images are taken before and after an intervention.

A preferred way of deriving the spectral model required the calculation of a clean HS representation of the biological tissue. This representation can be calculated by processing the HS data with a spectral signature of the at least one spectral confounder with the aim of minimising the variability caused by the spectral signature of the at least one spectral confounder.

The HS image comprises a plurality of images of the retina of the subject, each of the images being obtained at a distinct wavelength. The image may be pre-processed and the pre-processing can include, for example, a normalization of light intensities at the various wavelengths of the HS image. Image registration may take place to ensure that pixels of images taken at any given wavelength are aligned with corresponding pixels of images taken at any other wavelength so that corresponding pixels represent a same element of the retina of the subject. The registration can overcome misalignments caused by a movement of the eye of the subject as the images are taken at the various wavelengths.

The HS image of the retina may be segmented in order to identify a specific region of interest (ROI). For example, the segmentation may lead to selecting a specific region of a biological tissue, such as the retina, of the subject as the ROI when it is desired to determine whether or not amyloid beta is present in the tissue of the subject.

To study the variability of a specific spectral signal of a given group at different times, for example when images are taken before and after cataract surgery, to evaluate a specific confounder such as, in this example, discoloration of the natural lens, the specific spectral signal of this confounder may be removed in the evaluation of AD or of another disease. The variability of the specific spectral signal within a group of subjects having undergone cataract surgery can be determined, for example, using non-negative matrix factorization (NMF), principal component analysis (PCA), linear discrimination analysis (LDA), singular value discrimination (SVD) or unmixing. These techniques enable extracting meaningful spectral features from the HS images, these spectral features being related to the actual confounder (e.g. cataract) and explaining a large percentage of variability of HS image spectra. Effects of such spectral features can be eliminated from various HS images so that the resulting data can be evaluated for AD and/or other illnesses, the effects of the specific confounder being effectively minimized or removed.

To remove the effects of a specific confounder, a so-called "cube" is calculated. The cube is a representation of a HS image in which a plurality of single wavelength 2D images are stacked on top of one another, a third dimension being defined by the cumulative wavelengths of the images, thereby forming a 3D representation, or "cube".

HS imaging of the eye involves receiving spectral information from all the ocular structures the light interacts with before returning to the sensor. To reduce inter-subject, within subject, inter-session variability to determine the different biomarkers in the retinal tissue across the population, this allows for development as a proper screening tool and also use for longitudinal monitoring. Biomarkers include but are not limited to, varying levels of cataract and melanin content in the retina within the subject (within the eye and between the two eyes), and between subjects.

Figures 2A, 2B, 2C:
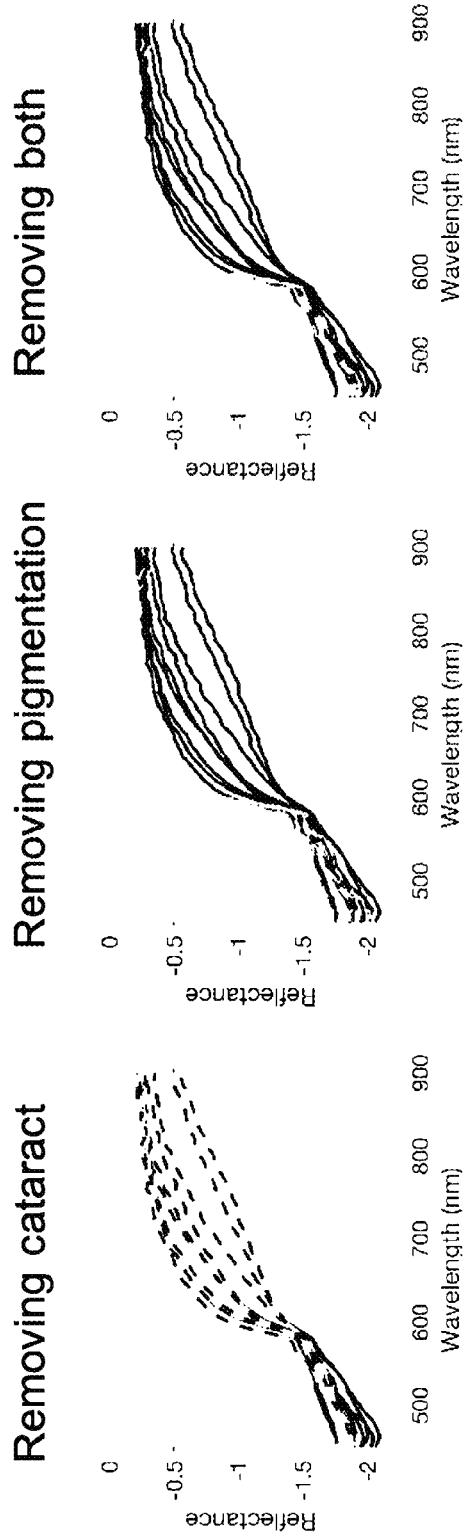
FIG. 2 shows spectral data before and after removing spectral effects from cataract and pigmentation.

Referring now to FIGS. 2A to 2C, the specific confounder corresponding to a cataract was obtained by imaging using the hyperspectral camera n=9 patients before and after undergoing cataract surgery. The hyperspectral images were co-registered so that the same pixels in both images corresponded to the same retinal locations. The HS image corresponding to the ratio before and after cataract surgery was computed and the resulting images were log transformed. Regions of the HS image with artifacts due or outliers were excluded and the remaining data fed into a principal component analysis. The principal axis responsible for most of the data variance was saved into memory.

The specific confounder corresponding to pigmentation was obtained by imaging n=7 healthy participants with various degrees of retinal pigmentation and no visible signs of a cataract on clinical examination. Spectral data from the hyperspectral images were combined, log transformed and fed into a principal component analysis. The principal axis responsible for the largest source of data variance was saved into memory.

Hyperspectral data from n=9 patients with various degrees of retinal pigmentation and visible cataract on clinical examination were acquired and log transformed (FIG. 2a to c, black curves). For each participant, the spectral data from the foveal region of the retina was sampled for illustration of the cleaning procedure. This spectral data was first projected orthogonal to the main spectral effect of cataract removal FIG. 2A), to the main spectral effect of retinal pigmentation removal (FIG. 2B), and to both spectral confounders (FIG. 2C).

Figure 3:
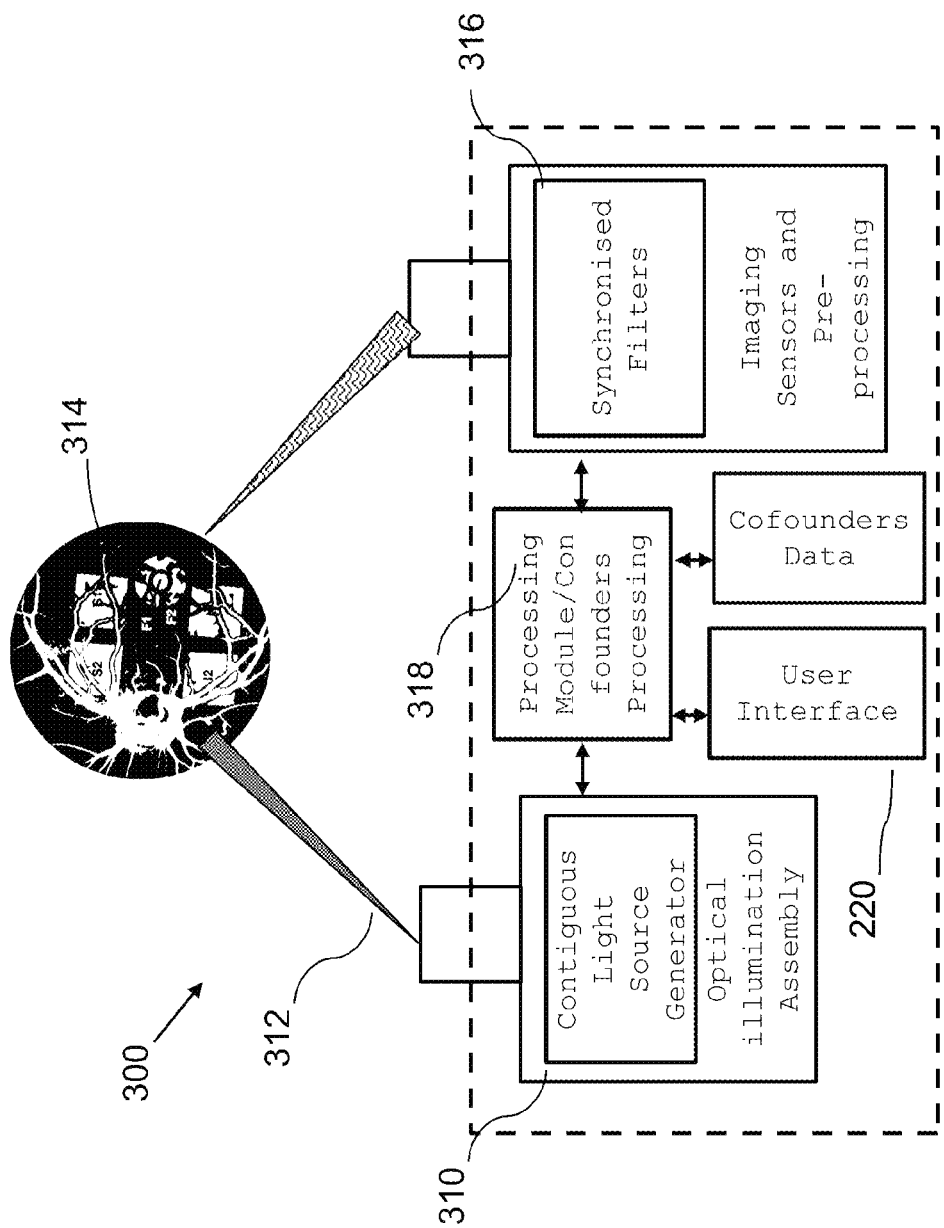
FIGS. 3 and 10 show schematic diagrams of systems for quantifying biomarker of a tissue.

Referring now to figure to FIG. 3, there is shown a schematic diagram of a system 300 for quantifying a biomarker of a biological tissue, based on HS imaging. The system has an optical illumination assembly 310 which provides illumination of a portion of a biological tissue with monochromatic light within a contiguous range of wavelengths. The optical assembly 310 comprises one or more light sources. For each wavelength, the generated light 312 is directed from the optical assembly 310 towards the biological tissue which, in the example of FIG. 2, is retinal tissue 314. For each wavelength, an imaging assembly 316 receives light reflected by the portion of the retinal tissue and translates the light to digital data.

A processing module 318 is provided to receive data from the imaging sensor 316 and combine and process the data received from the imaging sensor to extract spectral information and form a hyperspectral representation of the biological tissue. In addition, the processing module 318 retrieves, from a memory, a spectral signature of at least one image confounder and derives a spectral model of the biological tissue by processing the hyperspectral representation of the biological tissue and a spectral signature of the at least one spectral confounder. The spectral model is calculated by the processing module so that the correlation with the cofounder is minimized or, preferably, to be orthogonal to the identified spectral confounder. Furthermore, the processing module processes the hyperspectral representation of the biological tissue based on the spectral model to quantify the physiological parameter.

The processing module 318 can be configured to communicate with an external statistical database, through a communication interface and a communication network to retrieve spectral signatures of the at least one image confounder.

Whilst the imaging sensor module 316 shown in FIG. 3 includes synchronized filters, it should be appreciated that the filters could also be placed just after the contiguous light source, or elsewhere in the optical pathway.

The optical illumination assembly 310 can be configured to provide light between 400 nm to a 1000 nm. The light sources can be provided as wide band LEDs, a xenon flash light sources, tungsten sources, supercontinuum lasers and can be used in cooperation with wavelength selection mechanism, such as a synchronized filter.

Figure 4:
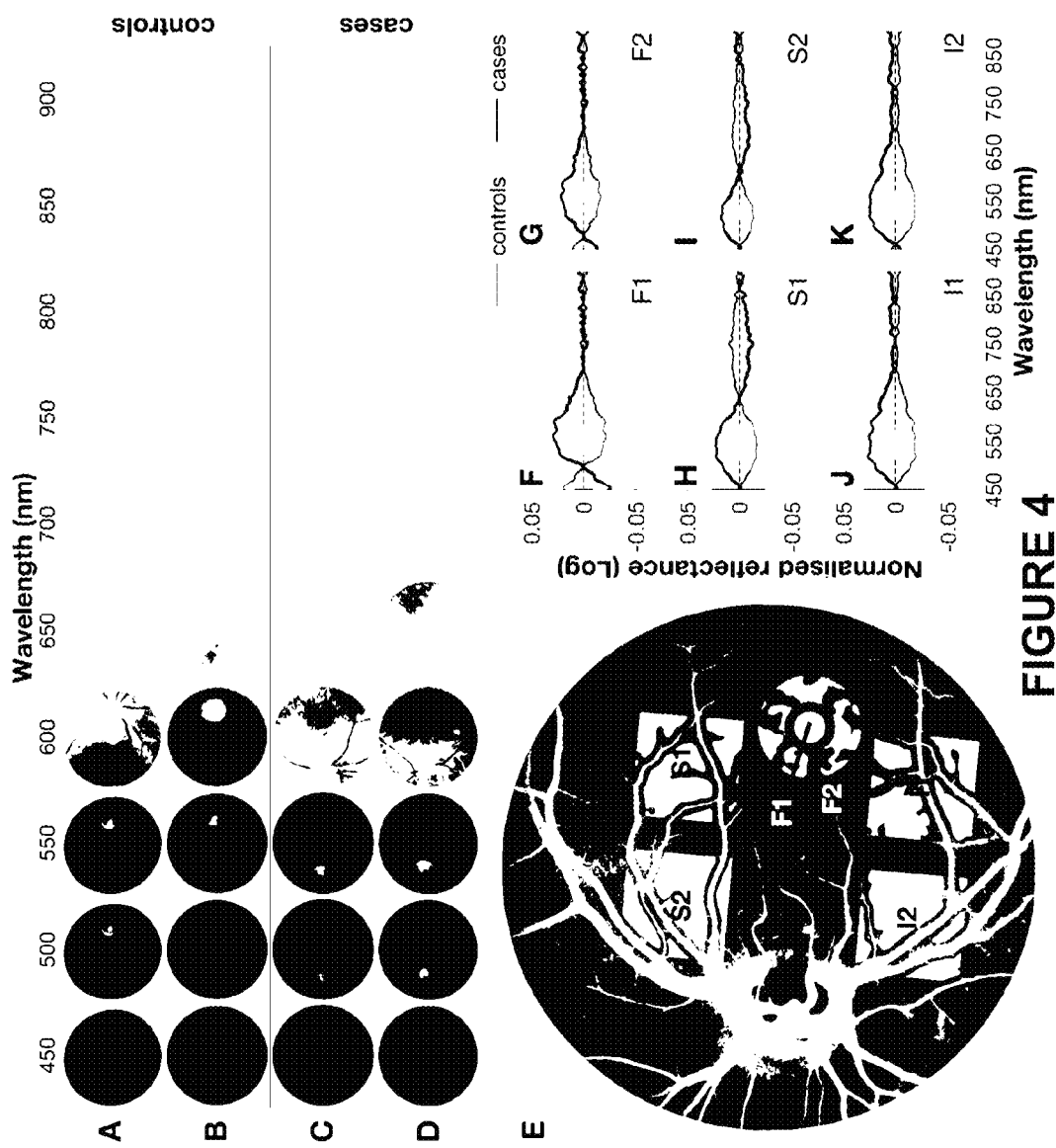
FIG. 4 shows representative HS montages of four eyes showing the inherent variability for individuals with positive brain amyloid beta PET scans (Alzheimer's disease) and those without (PET negative controls) data within- and between-eyes due the retinal and choroidal vasculature, ocular pigment and clarity of ocular media (A-D); the sampled foveal locations, superior & inferior to the temporal vascular arcades with segmentation of the major inner retinal blood vessels (E) and the normalized reflectance spectra at the different sampling locations for controls and cases (F to K)

Referring now to FIG. 4, there is shown the natural spectral variation between eyes that precludes discrimination between cases and controls with respect to amyloid beta status on PET. (A-D) Representative HS montages of 4 eyes (n=2 controls, n=2 cases from 450-900 nm in 5 nm steps) showing the inherent variability within- and between-eyes due to the retinal and choroidal vasculature, ocular pigment and clarity of ocular media. (E) Systematic sampling method used to analyse HS images including two foveal locations (F1, F2), superior (S1, S2) & inferior (I1,I2) to the temporal vascular arcades with segmentation of the major inner retinal blood vessels. (F-K) Normalised reflectance spectra at the different sampling locations for controls (n=20, darker) and cases (n=15, lighter) highlighting the large degree of inter-subject variability using uncorrected spectral data, which precludes discrimination between cases and controls. The data is shown as mean±SEM.

To account for within-subject variability and avoid selection bias, six regions of the retina based on well-defined anatomical landmarks were systematically sampled. The foveola was sampled using a circular area of interest (60-pixel diameter) centered on the fovea (F1). The parafoveola was sampled using an annulus (100-200 pixels in diameter) centered on the fovea (F2). Areas in the temporal vascular arcades superior (S1) and inferior to the fovea (I1) as well as superior (S2) and inferior to the optic nerve head (I2) were sampled using squares (200×200 pixels), on a fixed template horizontally orientated with the temporal raphe.

In each sampling location, blood vessels visible in the inner retina are automatically segmented using the green channel of the false-colored image. A difference of Gaussian (DoG) image was calculated using variance parameters 1 and 20 to increase contrast between the blood vessels and background whilst removing noise and artefacts. To be conservative, 40% of pixels in the DoG image with the highest intensity are considered to be blood vessels and were excluded from analysis. Reflectance spectra normalised to the average spectrum of a first cohort are displayed in figures F to K, highlighting the difference in spectra observed at the 6 sampling locations due to variations in retinal structures at each location. A large degree of inter-subject spectral variability is found. Although a trend can be observed in every location, no statistically significant difference is found between cases and controls on the basis of uncorrected reflectance data. These findings indicate that the effects of variability in key determinants of ocular reflectance must be accounted for before meaningful comparisons can be made between individuals.

Figure 5:
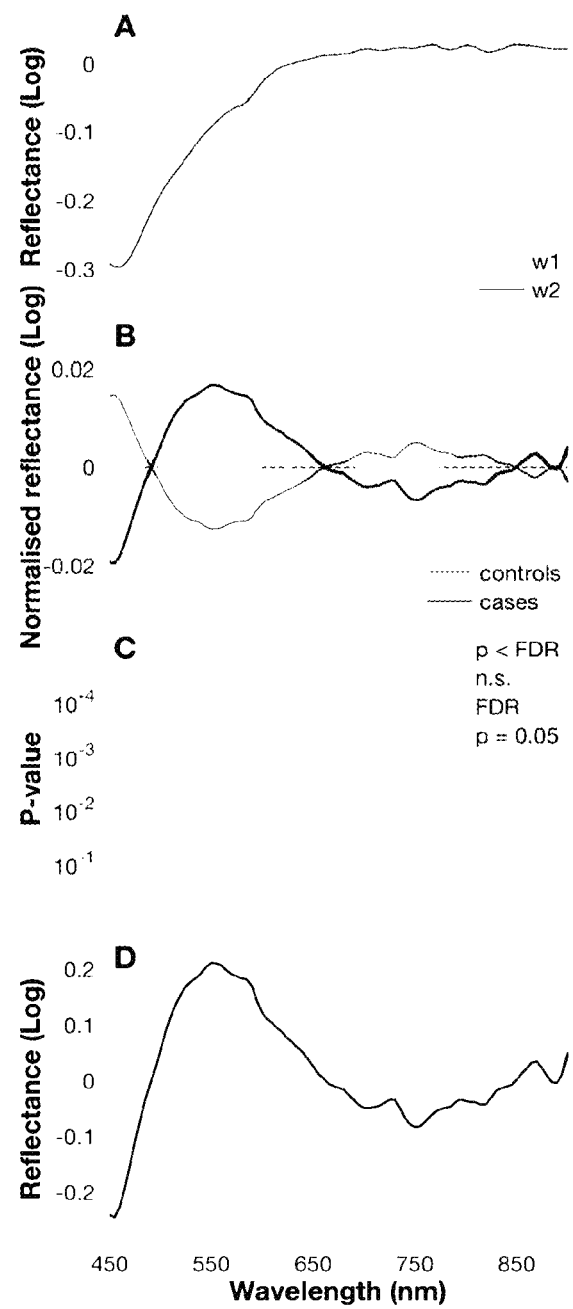
FIG. 5 shows a graph of the estimation of two main spectral confounders for retinal imaging data from individuals with positive brain amyloid beta PET scans (Alzheimer's disease) and those without (PET negative controls). (A), a graph showing the corrected reflectance spectra at a specified sampling location (B), a graph showing the P-values for two-sided unpaired t-tests between groups using false discovery rate control for significance across all the wavelengths (C), and a graph of the spectral model at the specified sampling location corresponding to the main spectral difference between the two groups (D)

Referring now to FIG. 5, there is shown how the spectral confounder and the spectral model are derived. (A) shows the estimation of two main spectral components of within-subject variability. These components could be largely explained by a combination of spectra from known ocular constituents and can be used to correct each reflectance spectrum. (B) depicts corrected reflectance spectra at sampling location S1 (n=20 controls, n=15 cases, data shown as mean±SEM) unmasked the spectral difference between the two groups. (C) shows P-values for two-sided unpaired t-tests between groups using false discovery rate (FDR) control for significance across all the wavelengths (n.s. stands for non-significant). And in (D) is depicted the spectral model at sampling location S1 corresponding to the main spectral difference between the two groups.

To transform the multiplicative interaction between retinal structure and reflectance, measured spectra can first be log-transformed. The average spectrum at each sampling location can then be computed and smoothed using spectral smoothing procedure such as a Savitzky-Golay filter with a $5^{th}$ order kernel of width of 13. At each location, a single HS score is obtained by combining the spectral variables using Dimension Reduction by Orthogonal Projection for Discrimination (DROP-D). This linear discrimination method was used to derive the HS scores as it is robust to over-fitting and well-suited to problems in which the number of observations (participants) is small compared to the number of variables (wavelengths). In brief, DROP-D works in two steps. First, it estimates (A) and removes (B) the main spectral axes of within-class variability from the data, i.e., spectral sources of variability that are detrimental to the discrimination problem. Second, it derives a model (D) by computing the principal spectral axis of between-class variability on the corrected data. A HS score (single number) for a given spectrum is obtained by taking its inner product with the spectral model. Note that by construction, the HS scores are not sensitive to any linear combination of the removed within-class axis. To further avoid over-fitting, leave-one-out cross-validation was used to identify the number of spectral axes to optimise discrimination between groups.

Figure 6:
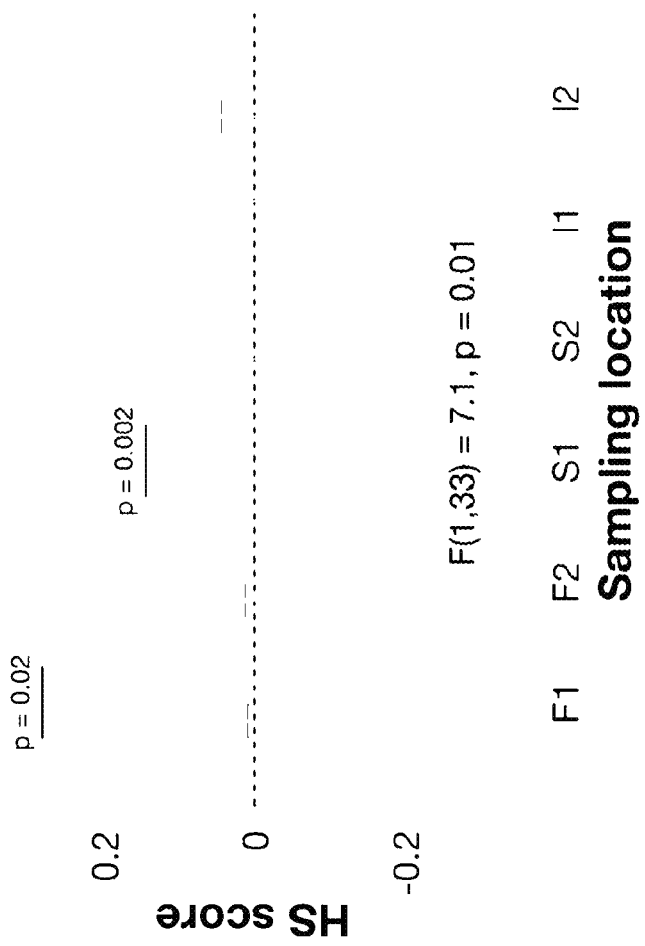
FIG. 6 shows a graph depicting the discrimination between individuals with positive brain amyloid beta PET scans (Alzheimer's disease) and those without (PET negative controls) using HS scores at the different sampling locations.

Referring now to FIG. 6 there is shown the discrimination between individuals with positive brain amyloid beta PET scans (Alzheimer's disease, cases) and those without (PET negative controls) using retinal HS scores. HS scores obtained at the different sampling locations were on average higher for the cases compared to controls (F1, 33=7.1, p=0.01, two-way repeated measures ANOVA). Error bars represent 95% Cl of the mean for each group. Pairwise comparisons show significant differences between sampling locations F1 and S1.

The spectral model derived for each sampling location was used to derive a HS score for each participant. Overall, these HS scores were higher in cases compared to controls across all retinal locations (F1, 33=7.1, p=0.01, two-way repeated measures ANOVA), indicating a general spectral difference between cases and controls, which was only visible after correcting for the inherent spectral variation between eyes.

Using pairwise comparisons at each location, it was shown that the greatest difference between groups was found at the S1 sampling location (p=0.002, 95% Cl: 0.06-0.22). This is consistent with the findings of post-mortem retinal immunohistochemical studies which indicate that amyloid beta accumulation appears the be greatest in the superior retina. Significant differences between cases and controls were also found at the F1 location.

Figure 7:
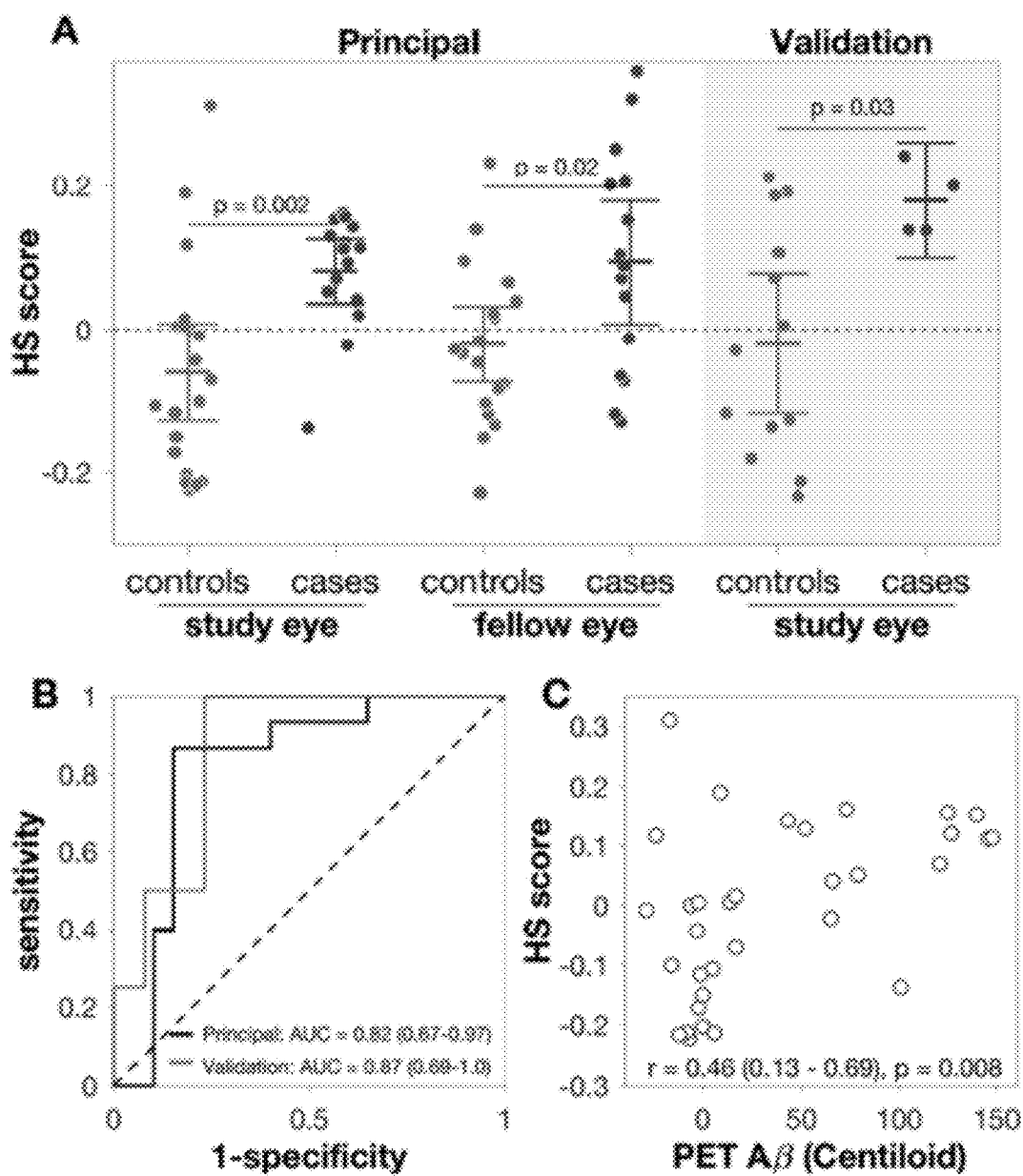
FIG. 7 shows graphs depicting how the HS scores are able to discriminate between individuals with positive brain amyloid beta PET scans (Alzheimer's disease) and those without (PET negative controls) in validation datasets.

Referring now to FIG. 7, there is shown how HS scores effectively discriminate between individuals with positive brain amyloid beta PET scans (Alzheimer's disease) and those without (PET negative controls) in validation datasets.

Validation of the spectral model. (A) Hyperspectral (HS) score obtained for each dataset (mean about 95% Cl for each group). HS images of the principal cohort (study eye and fellow eye) and the validation cohort were acquired on two different cameras of the same model, using the same imaging methods. Significant differences (two-sided unpaired t-tests controlled for false discovery rate for each dataset) were obtained between cases and controls in both cohorts. (B) Receiver operating characteristic curve (ROC) and area under the curve (AUC) for the principal cohort (black) and for the validation cohort (orange) show good discrimination between cases and controls. (C) Scatterplot of quantitative PET amyloid beta load and HS score showing significant positive correlation between the two metrics.

Figure 8:
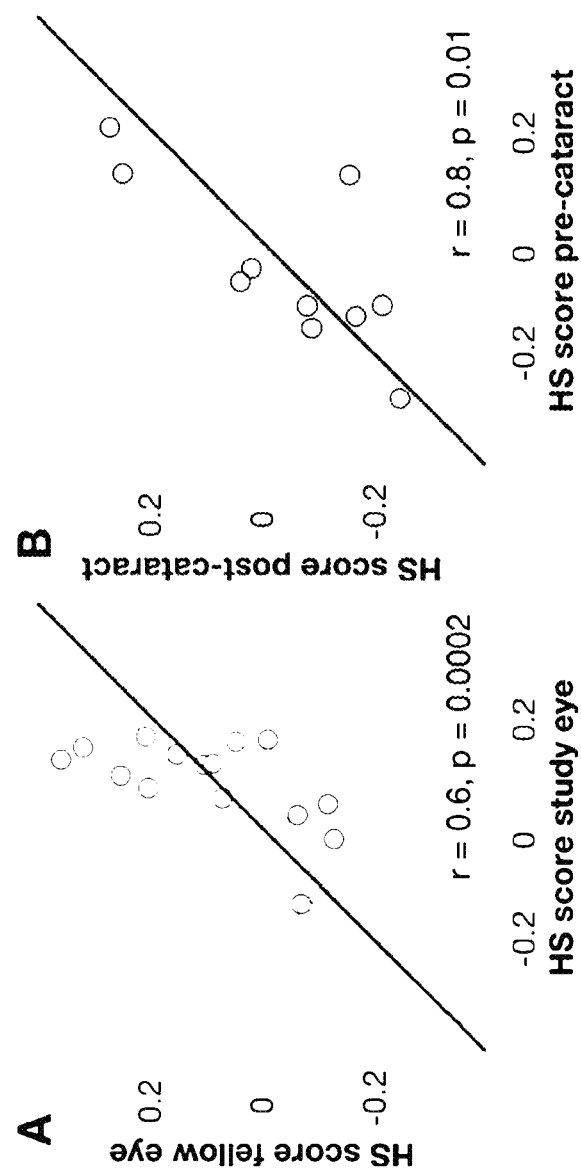
FIG. 8 shows in (A) correlation between HS scores of the study and fellow eye, and in (B) correlation between HS scores prior to and following cataract surgery.

Referring now to FIG. 8, there is shown robust agreement between eyes of the same individual despite lens status (presence of natural or artificial lens) following the application of the processing method described.

FIG. 8A depicts correlation showing a good agreement between the HS scores of the study and fellow eye. FIG. 8B depicts correlation showing good agreement between the HS scores pre- and post-cataract surgery for individuals, following the application of the processing method described.

To assess the robustness of the model to the presence of lens opacification (cataract) and artificial intraocular lenses, a cohort of 10 participants scheduled to undergo elective outpatient cataract surgery were studied. Retinal HS images were taken before and 8 weeks after cataract surgery. The spectral model obtained from the principal cohort was used to derive the HS scores pre- and post-cataract surgery. Differences in HS scores pre- and post-operatively were tested using a paired two-sided t-test. The agreement of the HS scores pre- and post-operatively was estimated using Pearson's correlation coefficient.

To test the robustness of the model, the HS scores from the study and fellow eyes of each individual in the principal cohort were correlated. In some individuals, the fellow eye had more ocular pathology (e.g., presence of drusen) than the study eye. Despite differences between some fellow and study eyes, there was a significant correlation (r=0.6, p=0.0002, 95% CI=0.32-0.78) between the HS scores for study and fellow eyes (FIG. 8A), indicating that the HS score is robust to a degree of variation in ocular pathology.

In addition to this, the effect of lens status on the HS score was investigated. Individuals undergoing routine surgery were recruited for visually significant cataracts and imaged them prior to and following cataract extraction and artificial intraocular lens implantation. No differences were found in HS score pre- and post-operatively (p=0.88, 95% CI=−0.15-0.18, two-sided paired t-test). Importantly, a strong correlation was found between HS scores measured pre- and post-operatively (r=0.8, p=0.01, 95% CI: 0.23-0.94, Figure panel B of FIG. 8), indicating that lens status (cataract or artificial intraocular lens) had minimal effect on HS scores.

Figure 9:
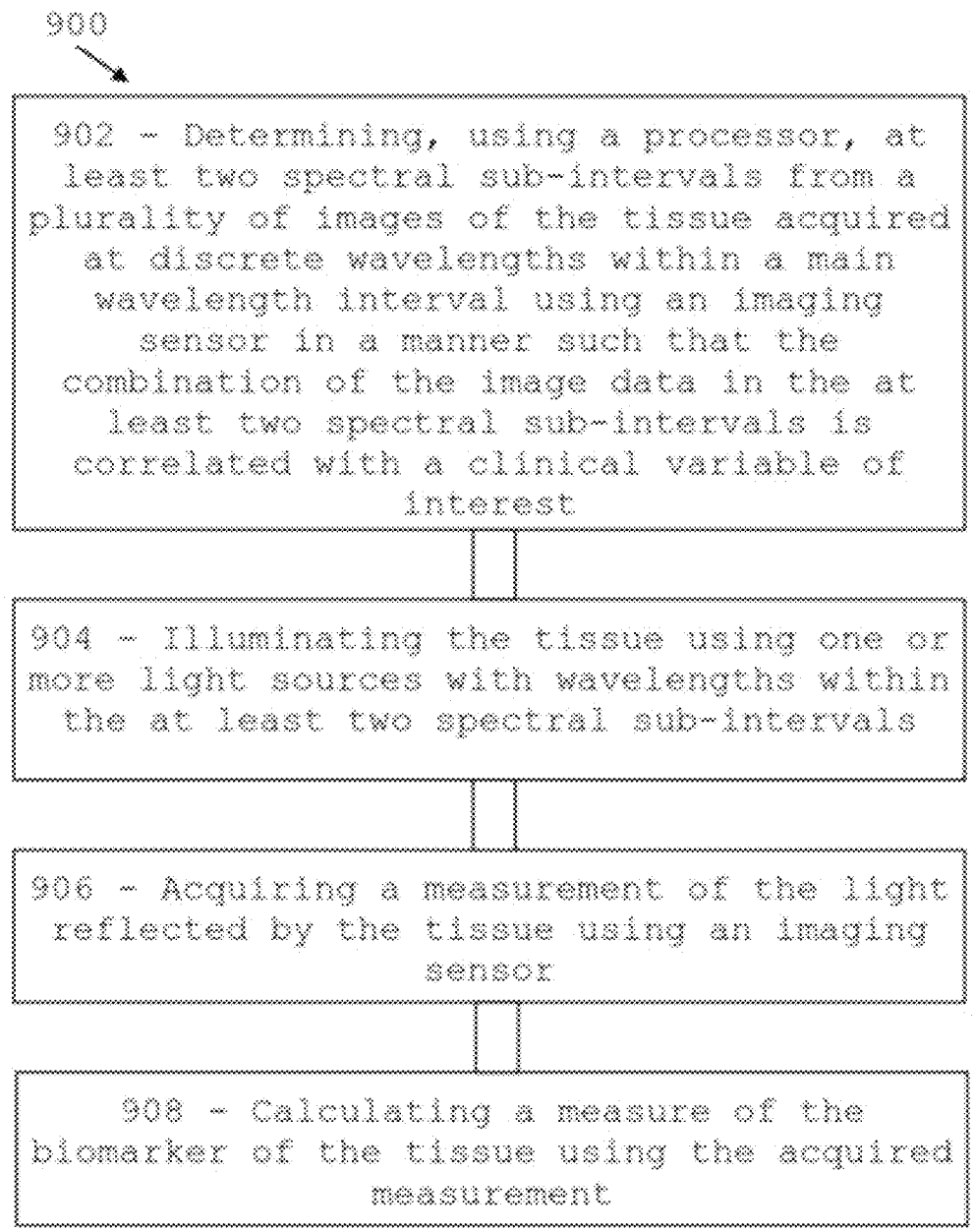
FIG. 9 shows a flow diagram with method steps used to quantify a biomarker of a biological tissue based on multispectral imaging.

Referring now to FIG. 9, there is shows a flow diagram 800 with method steps used to quantify a biomarker of a tissue based on multispectral imaging.

Multispectral imaging is used for detection of biomarker(s), e.g. amyloid in the retina. In some embodiments, multispectral imaging is advantageous in scaling down from HS imaging, for example, in the cost of device, in the complexity of data acquisition and data analysis.

At step 902 at least two spectral sub-intervals are determined, using a processor, from a plurality of images of the tissue acquired at discrete wavelengths within a main wavelength interval using an imaging sensor. The sub-intervals are determined so that the combination of the image data in the at least two spectral sub-intervals is correlated with a clinical variable of interest.

At step 904, the tissue is illuminated, using a one or more light sources with wavelengths within the at least two spectral sub-intervals. At step 906, an image of the reflected light is acquired using an imaging sensor. At step 908, a spectral parameter is extracted for each of the at least two spectral intervals to form a multispectral representation of the biological tissue. At step 910, a measure of the biomarker of the tissue is calculated using the acquired measurement.

The plurality of images of the tissue acquired at discrete wavelengths within a main wavelength interval could consist of one or more hyperspectral images of different participants and/or the same participant at different times. Extraction of spectral data from the image(s) with potential average over a predefined region of interest. Establishing one or more dependent variables using for example clinical data (e.g., burden of disease, presence or absence of disease) and/or demographic (e.g., age, sex) data. Feeding the spectral data and the dependent variables into an ADSF algorithm (and/or other variable/wavelength/spectral interval selection algorithms). The output of such algorithms corresponds to an optimized spectral interval(s) for a given prediction problem. Establishing the optimal combination of spectral interval which may involve using the dependent variables, statistical modeling techniques (multivariate regression, logistic regression, discriminant analysis or the like) and/or machine learning techniques (Support vector machine, Partial least squares, Artificial neural networks, or the like). The optimal combination may also involve the use of a previously recorded image, spatial information present in the image (segmentation of blood vessel, location of optic nerve head, fovea, texture analysis) or other images taken with other multispectral, hyperspectral or other medical imaging (e.g., OCT, PET scan) and non-imaging modalities, such as clinical data (age, blood pressure, questionnaires).

Figure 10:
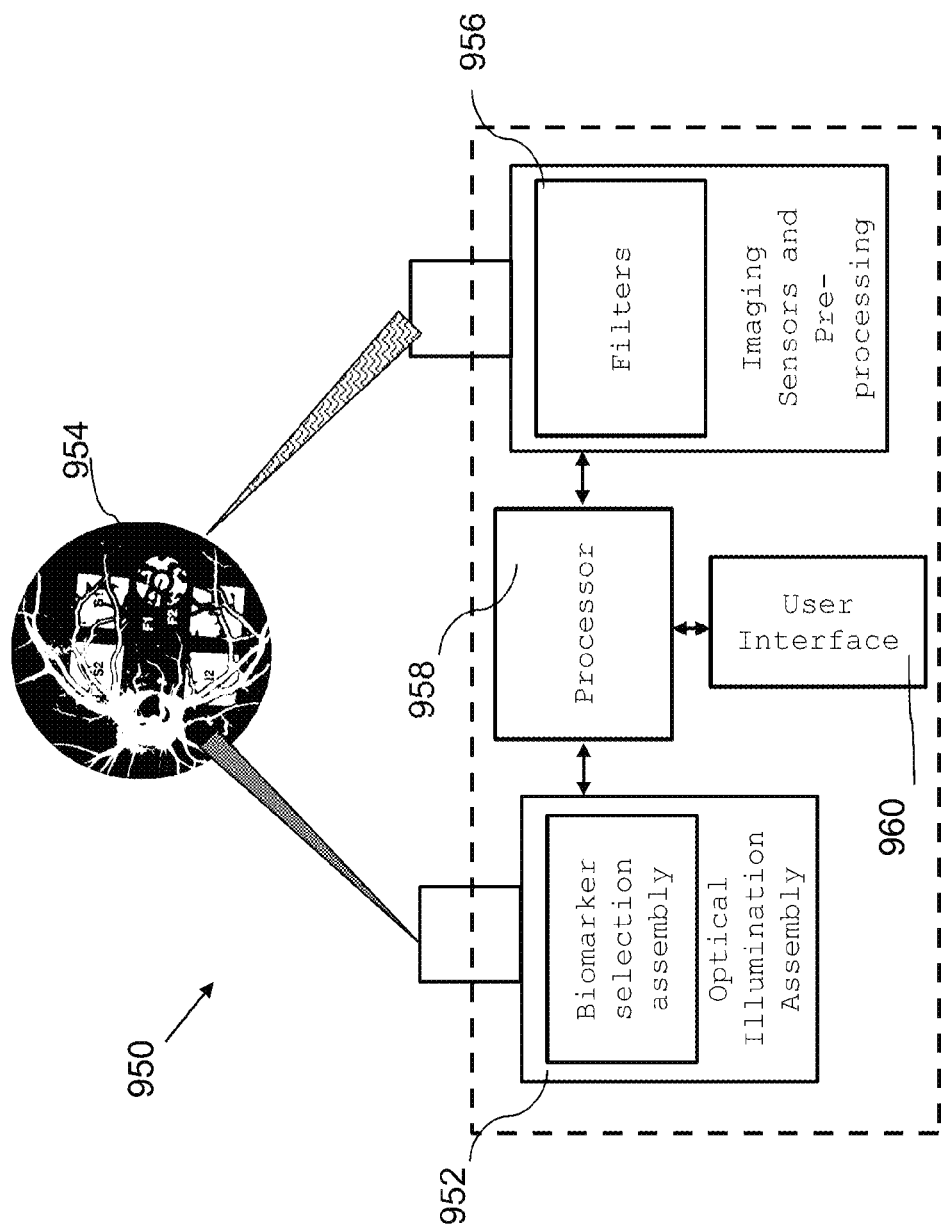

Referring now to FIG. 10, there is shown a schematic diagram of a system 950 for quantifying a physiological parameter of a biological tissue, based on multispectral imaging.

The system has an optical illumination assembly 952 which provides illumination to a portion of a biological tissue 954, in this case a portion of the retina of an eye. Assembly 952 comprises one or more light sources being arranged to illuminate a portion of the tissue at wavelengths within at least two predetermined spectral intervals.

The spectral intervals are selected by a biomarker selection assembly based on the biomarker being investigated. In some embodiments, the system may be setup with a specific optical illumination assembly suitable for investigating one or more specific biomarkers. In these instances the biomarker selection assembly is not present.

The generated light is directed from the illumination assembly 952 towards the biological tissue 954. For each wavelength, an imaging assembly 956 receives light reflected by the portion of the biological tissue and translates the light to digital data. The data can be locally processed by the system's processor 958 or made available for processing, in accordance with the methodologies described herein, by the system.

The system 950 may also be able to save image data locally and to a central database. The system may update the prediction capability (machine learning) with the accumulation of new data. The system may also be able to tell which multispectral filter is used/introduced at time of acquisition and send this information to the local/central database. The system may be able to measure/collect/store/transfer spectral and/or spatial calibration data. The system could have a subsystem to help alignment of the imaging system with the patient eye (with or without feedback to user and/or indication to move the camera in/out, left/right, up/down). The system may have a subsystem that manually or automatically focus the image of the retina received by the imaging sensor.

In some embodiments, retinal imaging using only selected wavebands may have potential to achieve similar results to HS imaging (i.e. confirmation of PET status/disease state). Thus, this may produce an opportunity to create a downscaled device but with similar capabilities of the HS camera at detecting biomarkers or diagnostic features of various diseases such as Alzheimer's disease.

Figure 11:
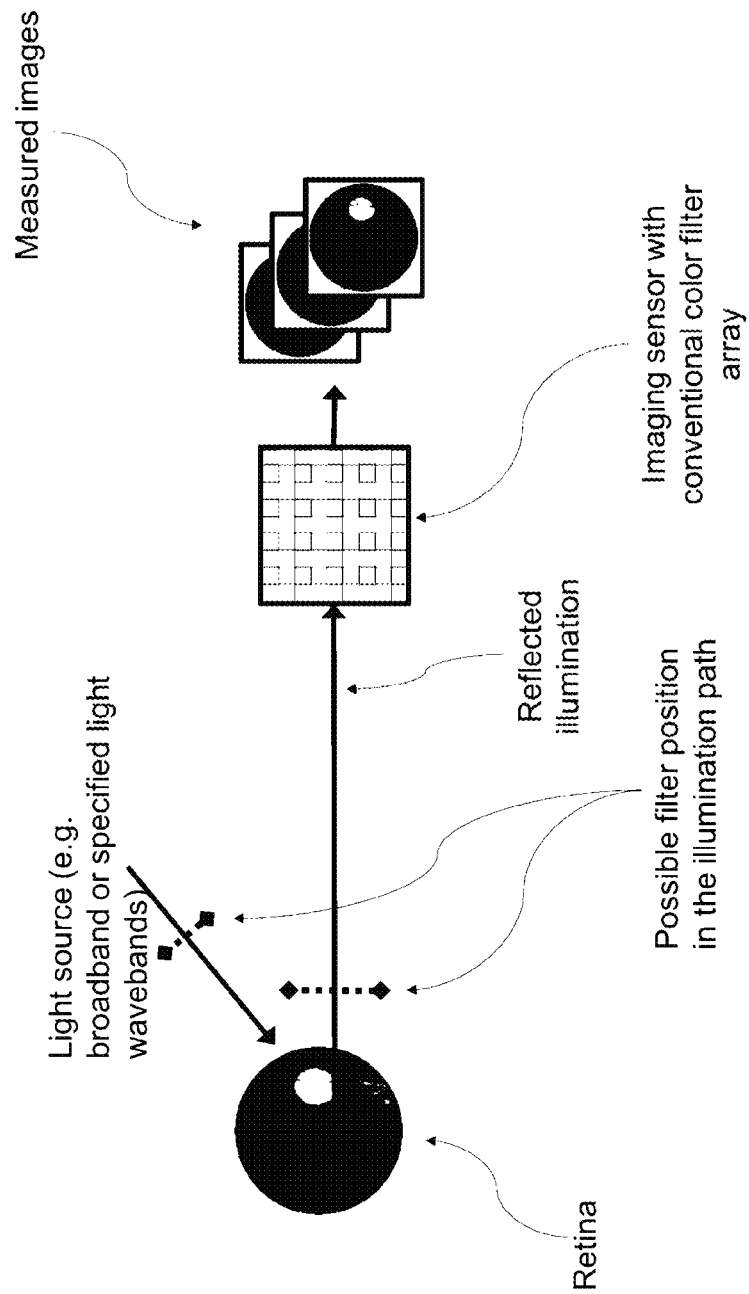
FIG. 11 shows a schematic diagram of retinal multispectral imaging with bandpass filter(s) in different positions in the optical light path of a fundus camera which has a broadband light source and a conventional color array at an imaging sensor.
Figure 12:
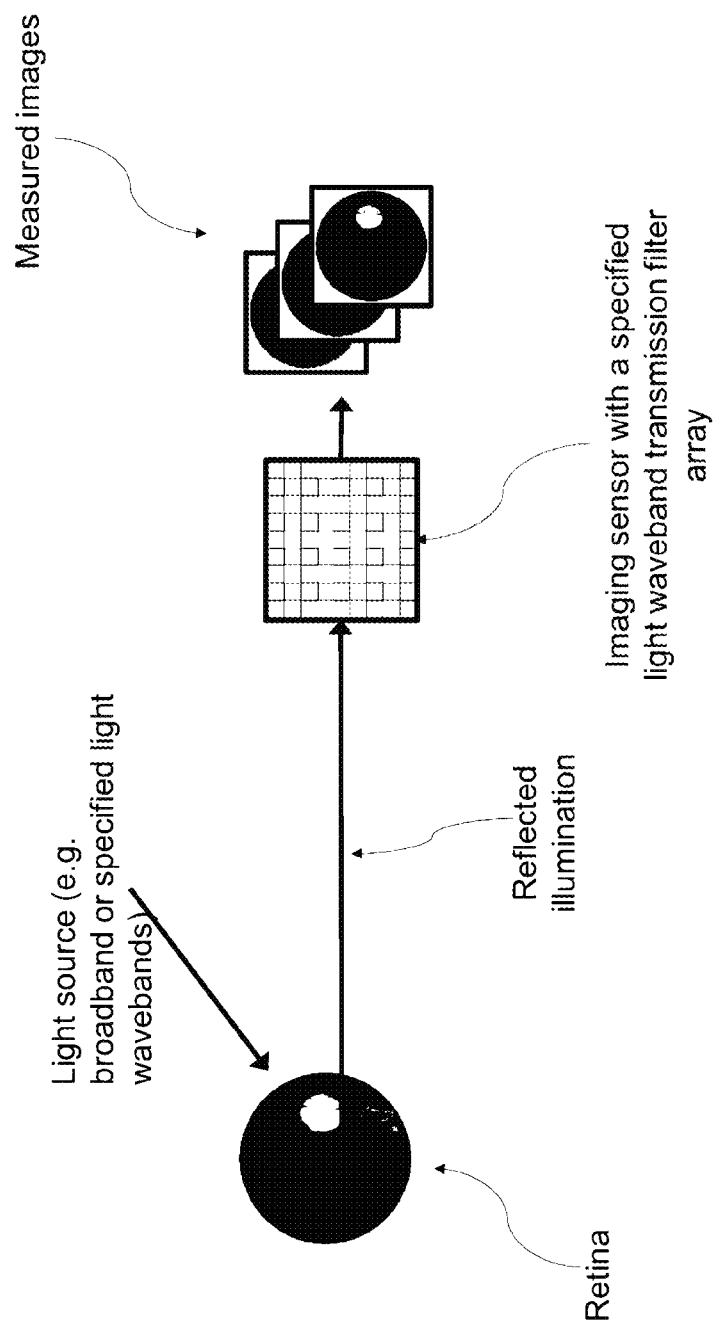
FIG. 12 shows a schematic diagram of retinal multispectral imaging using a light source and customized and modified filter array at an imaging sensor.
Figure 13:
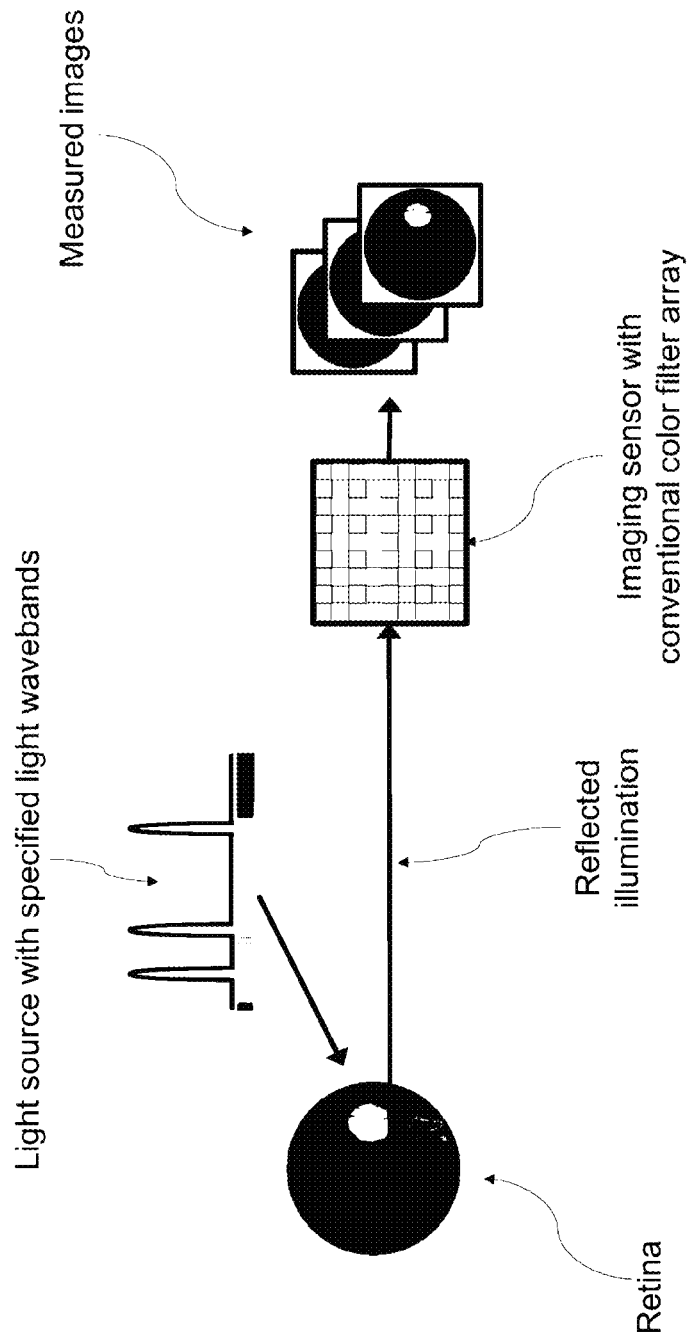
FIG. 13 shows a schematic diagram of retinal multispectral imaging using illumination with relatively narrow band(s) of light and a conventional color array at an imaging sensor.
Figure 14:
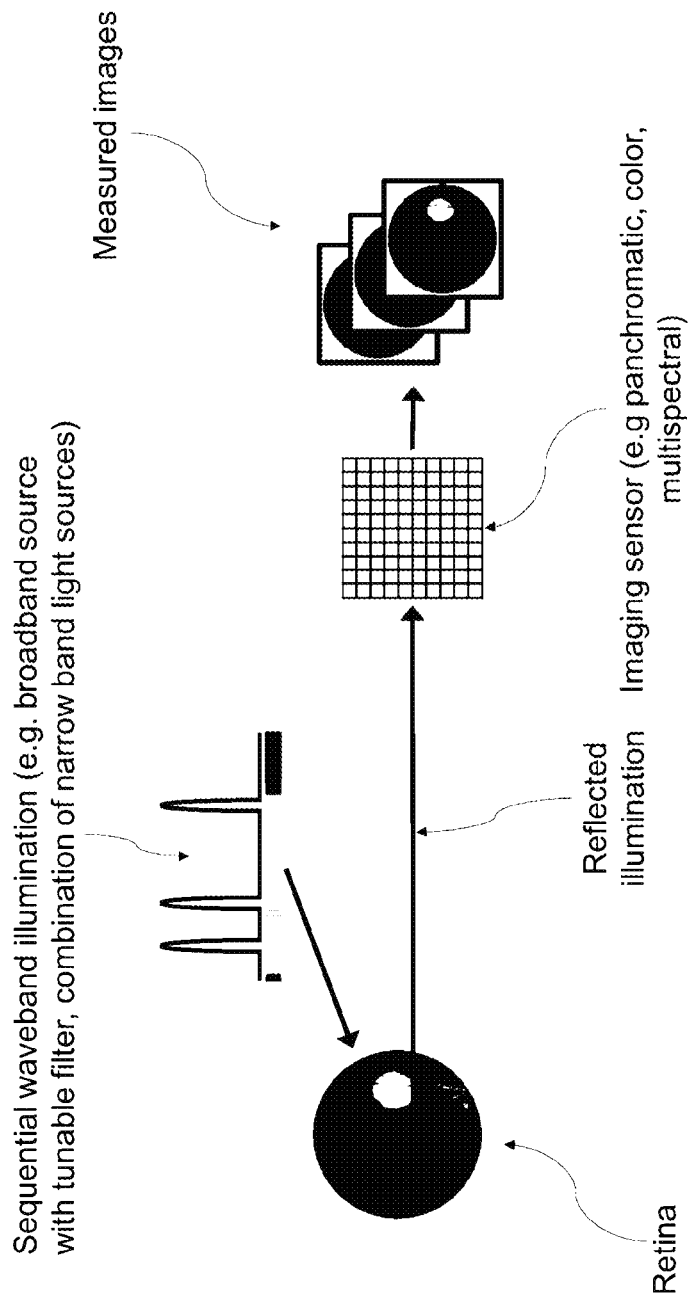
FIG. 14 shows a schematic diagram of retinal multispectral imaging using sequential waveband illumination with relatively narrow band(s) and an imaging sensor.

In some embodiments, the apparatus, device/camera, system, and method herein can acquire images at select wavebands. In some embodiments, the customized apparatus, device/camera, system, and method herein can acquire images at select wavebands, optionally with various options of improvements using existing devices/cameras. Nonlimiting examples of such improvements include: (1) adding onto an existing camera a custom filter set (e.g. a single multi bandpass filter or multiple filters allowing multiple bandpass at specified wavebands), which can be placed at but not limited to the positions along the optical path of the camera as shown in FIG. 11 (the filter(s) may be alternatively placed at other positions along the optical path including in a contact lens position of the cornea of an individual not shown in FIG. 11); (2) building a custom device/camera which for example may include any combinations of: (a) modified imaging sensor and/or modified color filter array, (b) modified light source, and/or (c) sequential waveband illumination as shown in FIGS. 12-14; and (3) a camera that is a combination of options from (1) and (2).

In some embodiments, one or more multispectral images using the different light wavebands can be combined and/or analysed together to improve diagnostic ability and/or robustness (e.g. an Alzheimer's disease filter for amyloid beta and an Alzheimer's disease filter for tau; an Alzheimer's disease filter for amyloid beta and a filter for different types of intraocular lenses).

In some embodiments, a measure of the biomarker (for example, a multispectral score) is obtained at the point of care, optionally within a short time period, using the devices, systems, and methods herein. In some embodiments, obtaining a measure of the biomarker includes acquiring one or more images of a subject's retina using the device/system herein and/or analyzing the image data acquired during a single or multiple imaging sessions if required. In some embodiments, the measure of the biomarker can be tracked over time by acquiring one or more images of a subject's retina using the device/system herein and/or analyzing the image data acquired over multiple imaging sessions if required. In some embodiments, such longitudinal studies over time may facilitate monitoring of progression of disease and/or evaluation of treatment over time.

In some embodiments, ADSF is used to determine the wavebands required from the raw reflectance hyperspectral data as shown in FIG. 15A. In this scenario for detection of amyloid in the retina, at least three wavebands are selected. The spectral information derived from these three bandpass filters of varying shape and width are combined in a weighted fashion (black trace) to derive a multispectral score. ADSF may not be the only method that can be used to determine the wavebands to use for multispectral imaging. Additionally, the shape/profile of the wavebands (e.g., an approximate Gaussian distribution), may change (as shown in FIG. 15B with the example of a rectangular-shaped band) as well as the number of wavebands required and its bandwidth (FIG. 15C) and/or center frequency can vary. In some cases, the wavebands, aside from differing in number may also have differing widths. In some embodiments, the wavebands may not overlap with each other as in FIGS. 15B-15C. In some embodiments, two or more of the light wavebands partially overlap e.g. Filters 1 and 2. In some embodiments, none of the specified light wavebands overlaps with other light wavebands. In some embodiments, none of the specified light wavebands comprises a center frequency that is approximately the same as another one of the specified light waveband. In some embodiments, the center frequency, and/or the full width half maximum bandwidth of each of the specified light wavebands varies based on population, age, presence of confounding factors or other factors. In some embodiments, the wavebands of filters are applied simultaneously during light generation, image acquisition. In some embodiments, the wavebands of filters are applied in sequence during light generation, image acquisition, or image analysis.

In some embodiments, the spectral information determined from these wavebands is mathematically combined in a weighted fashion. In some embodiments, a score (measure of the level of biomarker) is computed from the weighed combination to describe the spectral information from the selected wavebands, optionally in a single number. In this case of imaging Alzheimer's disease participants, the multispectral imaging score is linked to retinal amyloid beta load.

Figure 15:
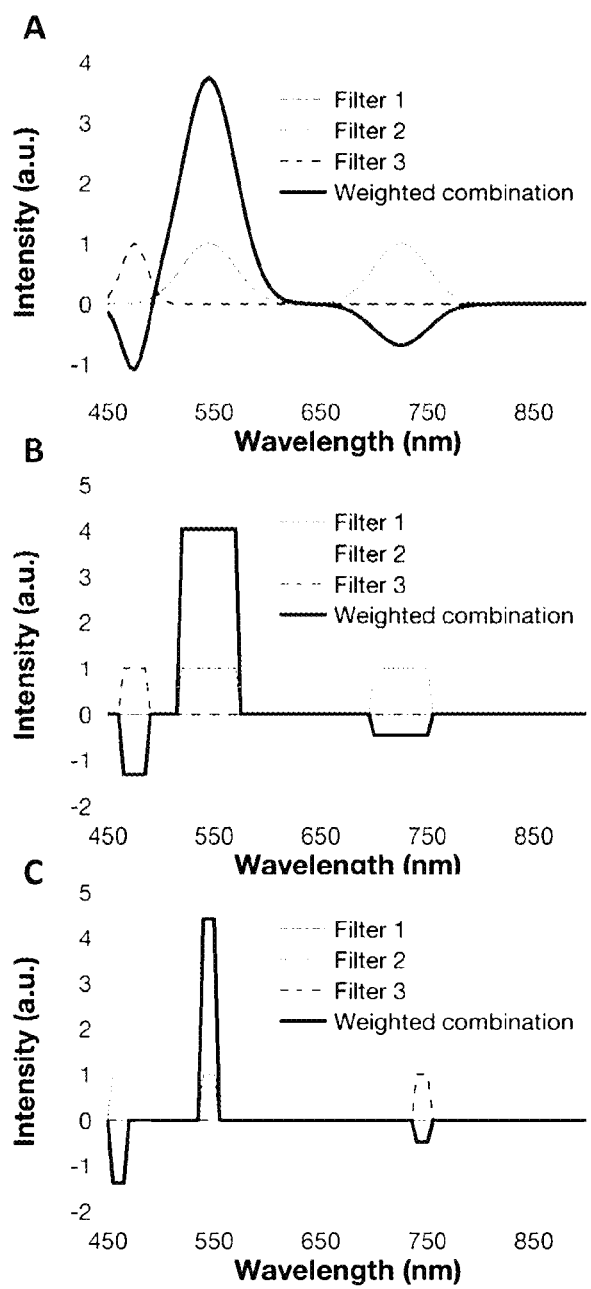
FIG. 15 shows selection of three wavebands for retinal multispectral imaging for Alzheimer's disease. ADSF showing which wavebands (Filter 1, 2, 3) are utilized in this scenario of detecting amyloid in the retina for the dataset examined.
Figure 16:
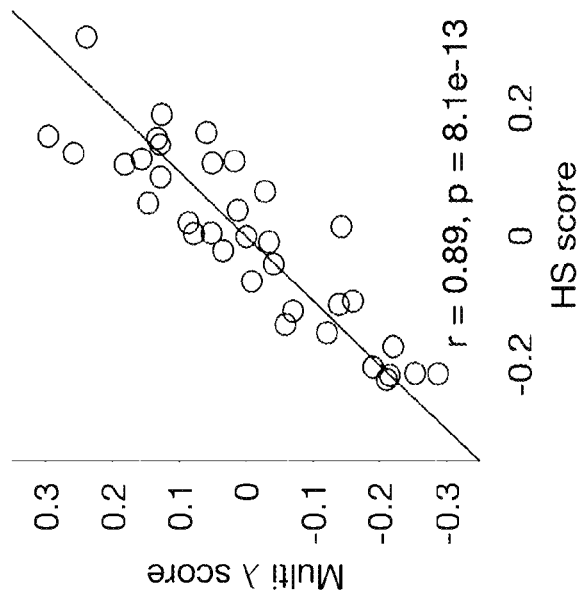
FIG. 16 shows association between scores obtained with hyperspectral (HS) and multispectral (MS) retinal imaging of individuals with positive brain amyloid beta PET scans (Alzheimer's disease) and those without (PET negative controls)

The computed biomarker levels can be compared to the HS scores as in FIG. 15. In this case, despite only using 3 wavebands to derive the the measure of biomarker levels from the raw reflectance data (using only a few select wavelengths with a wider band, the the measure of biomarker level closely resembles that derived using HS), strong agreement is found between the HS and multispectral imaging scores ($r=0.89$, $p=8.1\ e^{-13}$) suggesting that the the measure of biomarker level, herein as a downscaled version using spectral information from less wavelengths, is a good approximation of that derived from the full hyperspectral data.

Spectral changes occurring in a biological tissue such as the retina can be used to detect changes in a range of disease not limited to Alzheimer's disease. In some embodiments, the number/bandwidth of wavebands and the wavelengths may be the same or different to what can be used in multispectral imaging of AD. Other than AD, applications of multispectral imaging may include but are not limited to: detecting structural changes to retinal tissue in eye conditions such as (but not exclusive to) glaucoma, age-related macular degeneration and diabetic retinopathy. Multispectral imaging may also be used in other conditions such as Lewy body dementia, traumatic brain injury, Parkinson's disease, and detecting heavy metals in tissue and drug and/or toxin deposition.

In addition to the aforementioned embodiments, the inventors determined that increasing the contrast of the optic nerve neuroretinal rim (the neural tissue lining the edge of the optic disc with the cup in the centre) from the cup via multispectral imaging, allows for easier detection of tissue loss than conventional fundus photography for screening/ detection and longitudinal monitoring of diseases causing retinal nerve fibre layer loss such as, but not exclusive to, glaucoma.

Figures 17A, 17B, 17C:
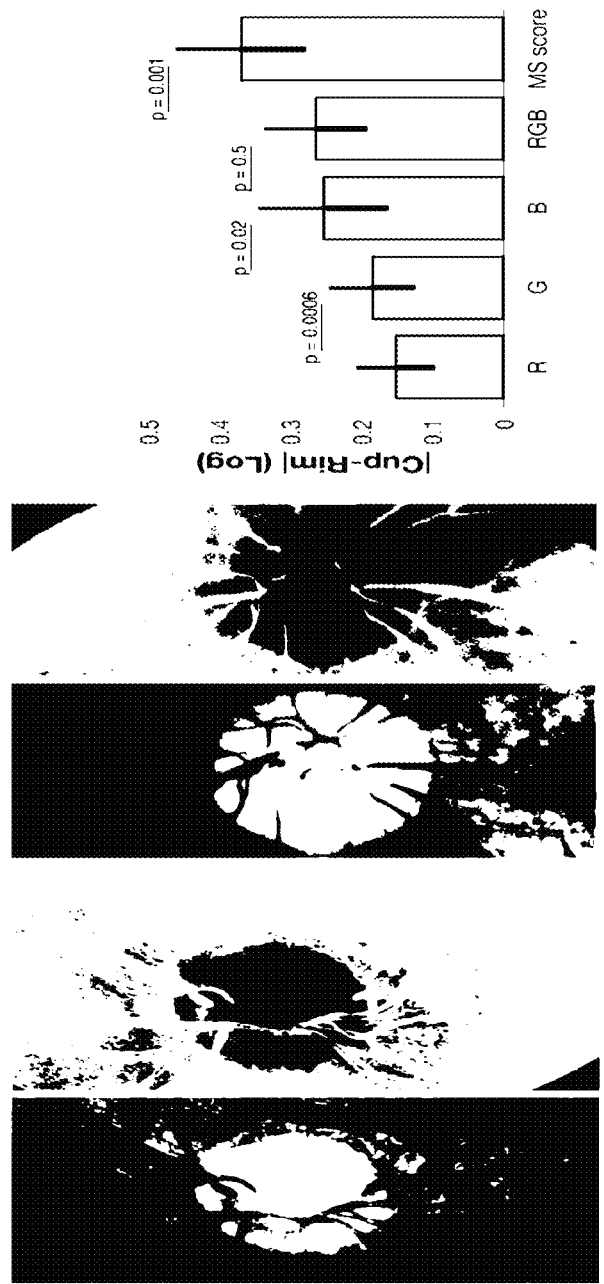
FIG. 17 shows the representation of contrast enhancement of the MS score image (right) compared to the conventional colour (RGB) image (left) respectively from two patients with glaucoma (A and B), and the comparisons of contrast enhancement achieved between the scores from each separate RGB colour channel from the conventional photograph, the score from the RGB fundus image, and the score from the MS image (C)

In this embodiment, hyperspectral images of $n=7$ patients with established glaucoma were taken. In each image the spectra for ten points on the neuroretinal rim and ten from the central cup were extracted. Using these spectra, it was estimated (using the ADSF method) which spectral intervals would be optimal for discriminating the neuroretinal rim from the cup. Spectral intervals were then selected from the hyperspectral image to obtain a multispectral image. Thereafter, the multispectral channels were combined to provide a score image exhibiting increased contrast between the neuroretinal rim and cup. FIGS. 17a and 17b each show a representation of the increased contrast of the neuroretinal rim which was derived from the MS score image compared to conventional fundus photography for two respective patients with glaucoma. Statistical comparisons of the change in contrast between neuroretinal rim and cup was performed between: each channel of the RGB image, the score image derived from combining the RGB channels and the score image derived from the multispectral image (FIG. 17c).

As is evident, in the conventional RGB image, the contrast is greater in the blue channel compared to the green and red. Combining the RGB channels together is only as good as the blue channel on its own. The MS image contrast is significantly larger than that obtained from the conventional RGB image, allowing for easier discrimination of the neuroretinal rim.

The inventors have found that the methodology in accordance with the invention can be used to estimate the RNFL tissue thickness from a multispectral image. To test the proposition, the retina of a patient with glaucoma was imaged with Optical Coherence Tomography (OCT) and the hyperspectral camera. The thickness of RNFL layer was segmented by the OCT camera software and as illustrated in FIG. 18a, a pseudo-coloured tissue thickness map was created of the OCT image (top left panel). This OCT-derived thickness map was co-registered with the hyperspectral image. Every pixel of the hyperspectral data for which an RNFL thickness was available from the OCT thickness map was extracted and fed into the ADSF method to estimate the 3 optimal spectral intervals for RNFL thickness estimation.

These spectral intervals were then selected from the hyperspectral image to obtain a multispectral image. Multivariate linear regression using the OCT thickness as the dependent variable and the channels of the MS image as explanatory variables was subsequently computed. FIG. 18b (bottom left panel) shows a pseudo-coloured map of the estimated RNFL thickness from the MS image is shown in the figure. FIG. 18c shows the pixel-wise correlation between the thickness measured by OCT and that estimated using MS imaging.

Figure 19A:
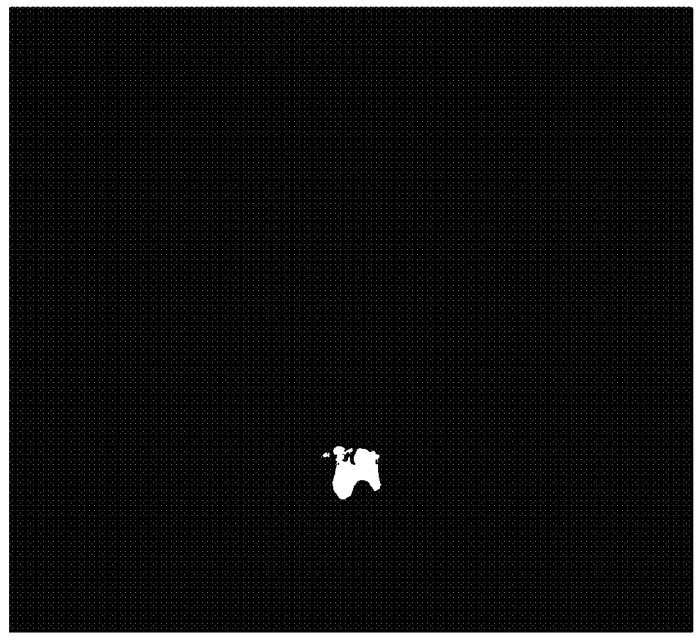
FIG. 19 shows that subretinal and intraretinal fluid is difficult to detect on conventional RGB fundus images as depicted in (A). Fluid is clearly apparent using MS imaging (B)
Figure 19B:

In a further embodiment of the invention, the inventors have determined that the methodology using MS imaging can be applied to detect retinal/subretinal fluid. To test the application of the methodology, a patient with diabetic retinopathy and retinal fluid, in the form of macular oedema, visible on OCT was imaged with the hyperspectral camera. Spectra were selected in the area where fluid was present (based on the OCT image) and in adjacent retinal tissue where there was not. The 3 spectral intervals that were optimal for increasing the visibility between retinal locations with and without fluid were selected using ADSF. A MS image was obtained from the hyperspectral image using these spectral intervals. A MS score image was computed by projecting the MS channels on the subspace that optimally discriminate between the affected and non-affected locations of the retina. FIG. 19a illustrates a conventional fundus image, as is evident, it is almost impossible to determine the location of fluid in the retina however as is clearly visible in FIG. 19b, it becomes obvious when observing the multispectral score image.

To test the proposition that the methodology was able to be used to validate new blood vessel growth originating from the choroid (choroidal neovascularization [CNV]), a patient with age-related macular degeneration (AMD) and CNV development, visible on a conventional OCT was imaged with the hyperspectral camera.

Figures 20A, 20B:
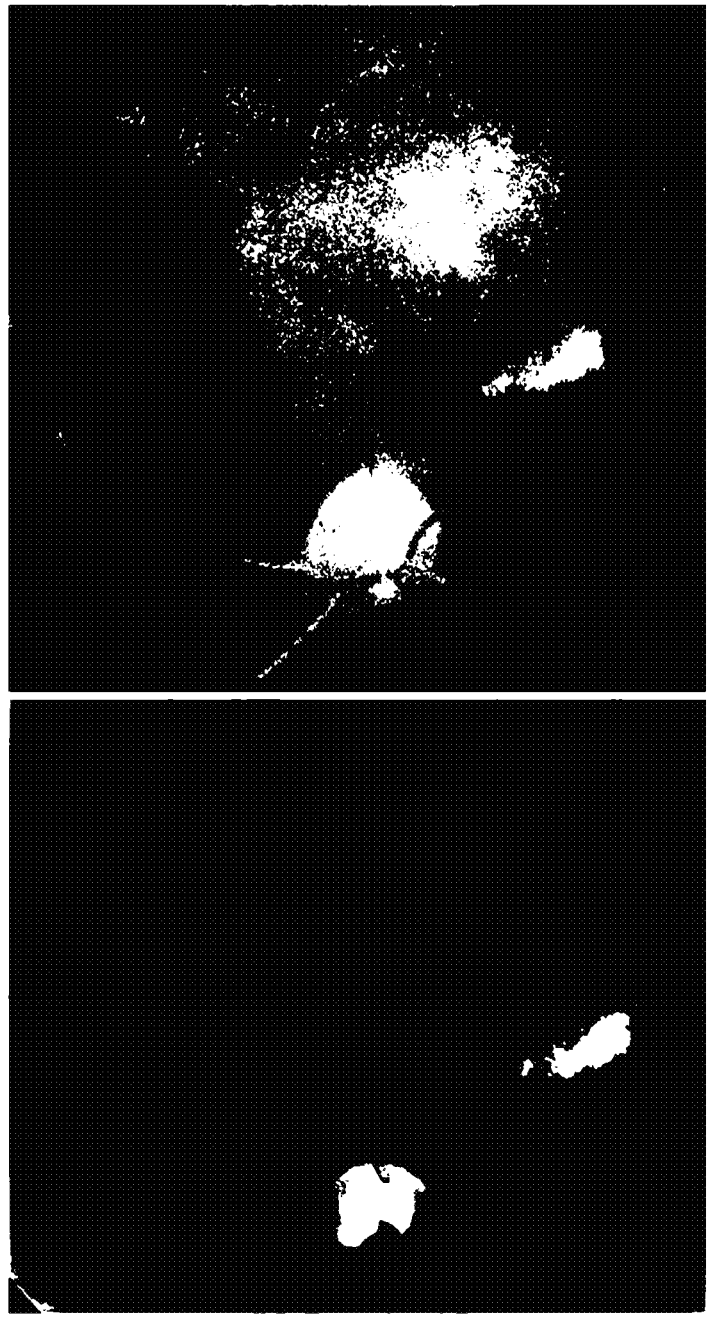
FIG. 20 shows that choroidal neovascularization (CNV) is often difficult to detect with conventional RGB fundus imaging as depicted in (A). CNV is more apparent using MS imaging (B)

Spectra were selected in the area where the CNV was present (based on OCT images) and in adjacent retinal tissue where CNV was absent. The 3 spectral intervals that were optimal for increasing the visibility between retinal locations with and without CNV were selected using ADSF. A MS image was obtained from the hyperspectral image using these spectral intervals. A MS score image was computed by projecting the MS channels on the subspace that optimally discriminated between the affected and non-affected locations of the retina. As depicted in FIG. 20a it is difficult to determine the location of CNV with conventional fundus photography but it becomes obvious when observing the multispectral score image (see FIG. 20b).

Figure 21:
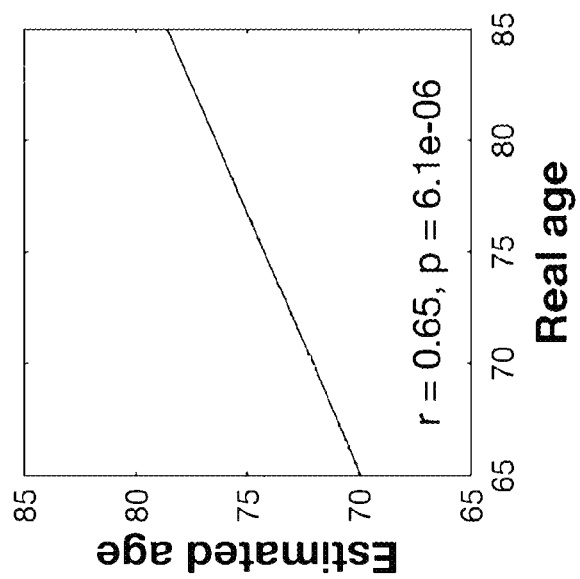
FIG. 21 is a graph depicting age prediction on the basis of retinal MS images.

In a still further embodiment, the methodology is able to be used to provide a retinal biomarker of ageing. To validate the application of the methodology, thirty nine patients were imaged using the hyperspectral camera. The average macular spectral data was extracted for each patient. The 4 spectral intervals that were optimal for predicting patients age were selected using ADSF. A MS image was then obtained from the hyperspectral image using these spectral intervals, and a MS score image was computed by projecting the MS channels on the subspace that was optimal for predicting the patient's age. The predicted age using the MS score at the sample location was used to create the illustrated prediction model shown in FIG. 21 which is plotted against the real patient's age.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer, a processor operatively connected to a memory, or a machine, those operations may be stored as a series of instructions readable by the machine, processor or computer, and may be stored on a non-transitory, tangible medium.

Systems and modules described herein may comprise software, firmware, hardware, or any combination(s) of software, firmware, or hardware suitable for the purposes described herein. Software and other modules may be executed by a processor and reside on a memory of servers, workstations, personal computers, computerized tablets, personal digital assistants (PDA), smartphone, and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

The present disclosure has been described in the foregoing specification by means of non-restrictive illustrative embodiments provided as examples. These illustrative embodiments may be modified at will. The scope of the claims should not be limited by the embodiments set forth in the examples, but should be given the broadest interpretation consistent with the description as a whole.

TERMS AND DEFINITIONS

Clinical variable: any measurable characteristic or property of an individual that relates to a physiological, pathological or disease state including disease subtype or severity and that can have different quantitative or qualitative values between and within individuals. Clinical variables may be used to make clinical decisions for people with a given disease.

Biomarker: an indicator of some biological state or condition by which a particular pathological or physiological process or disease that can be identified or measured.

Hyperspectral imaging (HS): where each pixel in an image acquires the light intensity for a large number (can be dozens to thousands) of contiguous, narrow (<20 nm) equally-spaced wavelength bands such that each pixel contains a continuous spectrum.

Multispectral imaging (MS): refers to imaging using more than 1 wavelength band of a certain bandwidth. These bands need not be equally wide or equally spaced bands unlike hyperspectral imaging.

Wavebands: bands of light at a certain range of wavelengths that has a certain bandwidth and a center frequency.

Multi bandpass filter: a bandpass filter, bandstop filter(s), or a combination of multiple filters allowing desired multiple wavebands through.

Multispectral imaging score (a nonlimiting example of the measure of biomarker level): Multispectral score is a linear or non-linear combination of weighted spectral information from select wavebands of light.

ADSF: Application Dedicated for Selection of Filters, algorithm used to select optimal wavelengths for a particular application (in this case, wavelength selection for multispectral imaging for detection of amyloid in the retina). This may not be the only method that can be used to determine the optimal wavelengths to use. Additionally, the shape of the wavebands may vary.

AD: Alzheimer's disease.

PET: positron emission tomography.

PET Centiloid: Centiloid is the generic score to combine the SUVR (standardized uptake value ratio) results derived from different radioactive tracers used in PET imaging so that meaningful comparisons could be made.

Aβ: amyloid beta, a protein known to be present in Alzheimer's disease.

AUC: area under the curve of receiver operating characteristic curves.

The invention claimed is:

1. A method for quantifying a biomarker of a tissue, the method comprising:
receiving data comprising light reflectance data from the tissue at a plurality of wavelengths within a main wavelength interval acquired by an imaging sensor;
determining, using a processor, at least two spectral sub-intervals within the main wavelength interval in a manner such that a combination of the light reflectance data in the at least two spectral sub-intervals is correlated with a clinical variable of interest;
receiving, at least one spectral confounder present in the tissue causing a spectral variability in the light reflectance data;
extracting spectral features related to the spectral confounder from the light reflectance data; and
calculating a measure of the biomarker of the tissue using the light reflectance data in the at least two spectral sub-intervals using the processor;
wherein the main wavelength interval is broader than each of the at least two spectral sub-intervals.

2. The method of claim 1, wherein the received light reflectance data is obtained by illuminating the tissue using one or more light sources with wavelengths within the main wavelength interval.

3. The method of claim 1, wherein the clinical variable of interest comprises any one or a combination of a disease, a severity or subtype of disease, a known biomarker or a physiological state.

4. The method of claim 1, wherein the clinical variable of interest comprises the amount or distribution of amyloid beta measured in a brain using positron emission tomography (PET), or measured in cerebrospinal fluid (CSF).

5. The method of claim 1, wherein identifying at least one spectral confounder comprises reading from a spectral database one or more spectral profiles of spectral confounders.

6. The method of claim 1, wherein the at least one spectral confounder comprises at least one ocular confounder and the quantified biomarker indicates the presence or absence of a variable of interest in the retina of the person.

7. The method of claim 1, wherein the at least two spectral sub-intervals span the entire main wavelength interval such that the received light reflectance data represents a hyperspectral representation of the tissue.

8. The method of claim 7 comprising the steps:
deriving a spectral model of the tissue such that the coupling of the spectral model and the identified spectral confounder is substantially reduced; and
calculating a measure of the biomarker of the tissue using the derived spectral model.

9. The method of claim 8 wherein the substantial coupling reduction is achieved by deriving the spectral model of the tissue to be orthogonal, uncorrelated or independent to the identified spectral confounder.

10. The method of claim 8, wherein deriving a spectral model of the tissue comprises deriving a clean hyperspectral representation of the tissue by processing the hyperspectral representation of the tissue and a spectral signature of the at least one spectral confounder in a manner such that the clean hyperspectral representation of the tissue has reduced variability caused by the spectral signature of the at least one spectral confounder.

11. The method of claim 10, wherein deriving a clean hyperspectral representation comprises removing, from the spectral information, a spectral variability caused by the spectral profile of the at least one spectral confounder.

12. The method of claim 8, wherein the spectral model is derived from the main spectral difference between two groups, each group having a distinct amount of the variable of interest.

13. The method of claim 1, wherein the at least two sub-intervals included in the main wavelength interval are defined such that the received data represents a multispectral representation of the tissue.

14. The method of claim 13, wherein determining at least two spectral sub-intervals is performed in a manner such that the spectral information of the combination of the at least two spectral sub-intervals and the spectral confounder are orthogonal, uncorrelated or independent.

15. The method of claim 13, wherein determining at least two spectral sub-intervals is performed by applying a band selection method, a machine learning algorithm or an artificial intelligence engine on an initial dataset containing a larger set of spectral sub-intervals.

16. The method of claim 1, wherein determining at least two spectral sub-intervals is performed by a machine learning algorithm that transforms the light reflectance data in the at least two spectral sub-intervals into a score that represents the biomarker.

17. The method of claim 16, wherein the machine learning algorithm accounts for demographic information, clinical information, other variables of interest or multiple regions of interest in the received light reflectance data.

18. A system for quantifying a biomarker of a tissue using light reflectance data, the system comprising:
- an optical assembly comprising one or more light sources arranged to illuminate a portion of the tissue at wavelengths with light within at least two selected spectral sub-intervals;
- an imaging assembly comprising an imaging sensor arranged to receive light reflected from the portion of the tissue and translate the light to digital data; and
- a processing module arranged to receive data from the imaging sensor and being configured to:
  - retrieve, from a memory, a spectral signature of at least one spectral confounder present in the tissue causing a spectral variability in the light reflectance data;
  - combine and process the data received from the imaging sensor and the spectral signature of the at least one spectral confounder to extract spectral information and form a multispectral or hyperspectral representation of the tissue;
  - extract spectral features related to the at least one spectral confounder from the light reflectance data; and
  - process the multispectral or hyperspectral representation of the tissue to quantify the biomarker;

wherein the at least two selected spectral sub-intervals are specific to a known variable of interest and wherein at least one spectral confounder causing a spectral variability of the received data is present in the tissue.

19. The system of claim 18, wherein the optical assembly comprises one or more optical filters arranged to filter the light along a generated light path or a reflected light path within the at least two sub-spectral intervals.

20. The system of claim 18, wherein the tissue is a portion of the retina and the variable of interest is brain or cerebrospinal fluid amyloid beta level related to Alzheimer's disease and the at least two selected spectral sub-intervals consist of three wavebands located within about 100 nm of 475 nm, within about 100 nm of 545 nm, and within about 100 nm of 725 nm, and each with a bandwidth under about 200 nm.

21. The system of claim 18 wherein the illumination assembly is arranged to successively illuminate a portion of a tissue with monochromatic light within a contiguous range of wavelengths.

* * * * *